United States Patent [19]
Appleby et al.

[11] Patent Number: 6,124,363
[45] Date of Patent: Sep. 26, 2000

[54] DOFETILIDE POLYMORPHS

[75] Inventors: Ian Colin Appleby; Trevor Jack Newbury; Gary Nichols, all of Sandwich, United Kingdom

[73] Assignee: Pfizer Inc., New York, N.Y.

[21] Appl. No.: 09/423,986

[22] PCT Filed: Oct. 9, 1998

[86] PCT No.: PCT/EP98/06641

§ 371 Date: Nov. 16, 1999

§ 102(e) Date: Nov. 16, 1999

[87] PCT Pub. No.: WO99/21829

PCT Pub. Date: May 6, 1999

[30] Foreign Application Priority Data

Oct. 27, 1997 [GB] United Kingdom .................. 9722662

[51] Int. Cl.⁷ .................. A61K 31/18; C07C 303/44; C07C 311/11

[52] U.S. Cl. .................. 514/605; 514/821; 564/82

[58] Field of Search .................. 564/82; 514/605, 514/821

[56] References Cited

FOREIGN PATENT DOCUMENTS 0245997  11/1987  European Pat. Off. .
0898964   3/1999  European Pat. Off. .

OTHER PUBLICATIONS

E. M. Vaughan Williams, "Antiarrhythmic Action and the puzzle of perhexiline–5. Class 3 antiarrhythmic action" Academic Press, 1980, p. 26–31.

*Primary Examiner*—Peter O'Sullivan
*Attorney, Agent, or Firm*—Peter C. Richardson; Gregg C. Benson; A. Dean Olson

[57] ABSTRACT

The invention relates to the substantially pure dofetilide polymorphs P162, P162a and P143, and to processes for the preparation of, compositions containing and to the uses of, such polymorphs.

29 Claims, 33 Drawing Sheets

PXRD pattern of dofetilide polymorph P162b

PXRD pattern of Reference Example 1

* Peaks due to dofetilide polymorph P162b.

PXRD pattern of Reference Example 1A

PXRD pattern of Reference Example 2

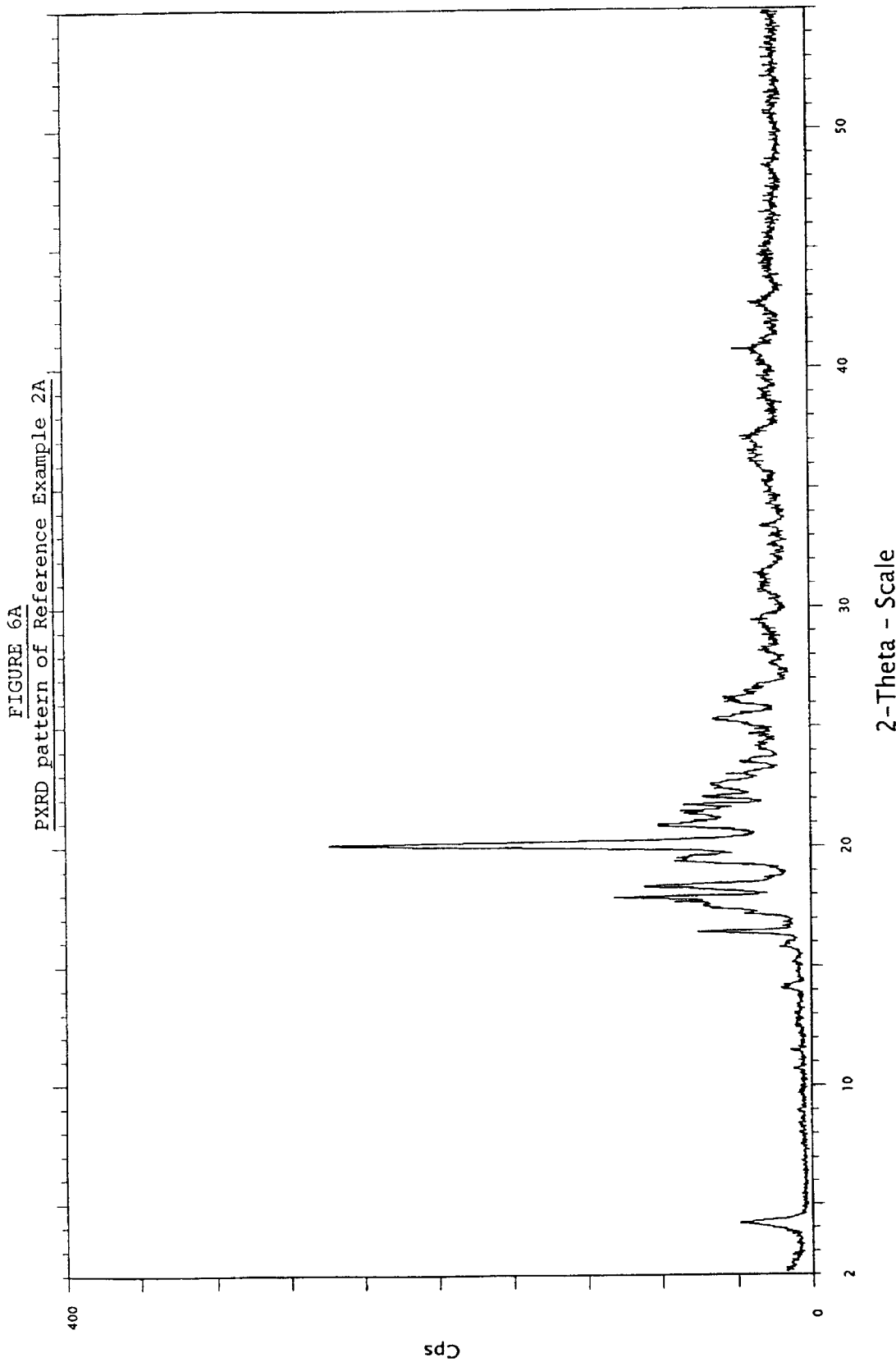

PXRD pattern of Reference Example 3

PXRD pattern of Reference Example 3A

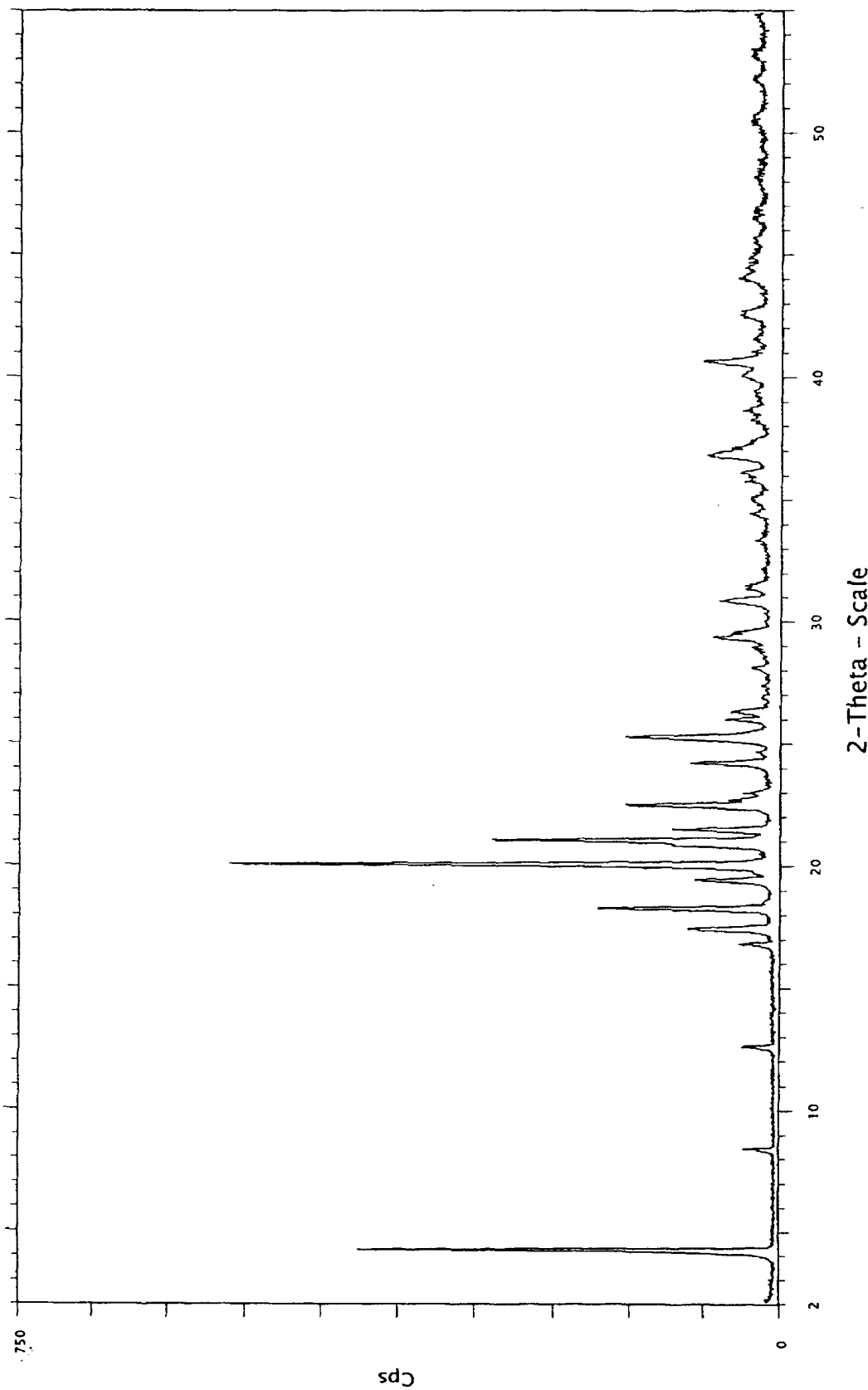

PXRD pattern of Example 7

PXRD pattern of Example 8

DSC thermogram for dofetilide polymorph P162

DSC thermogram for dofetilide polymorph P162a

DSC thermogram for dofetilide polymorph P143

DSC thermogram for Reference Example 1

DSC thermogram for Reference Example 1A

DSC thermogram for Reference Example 2

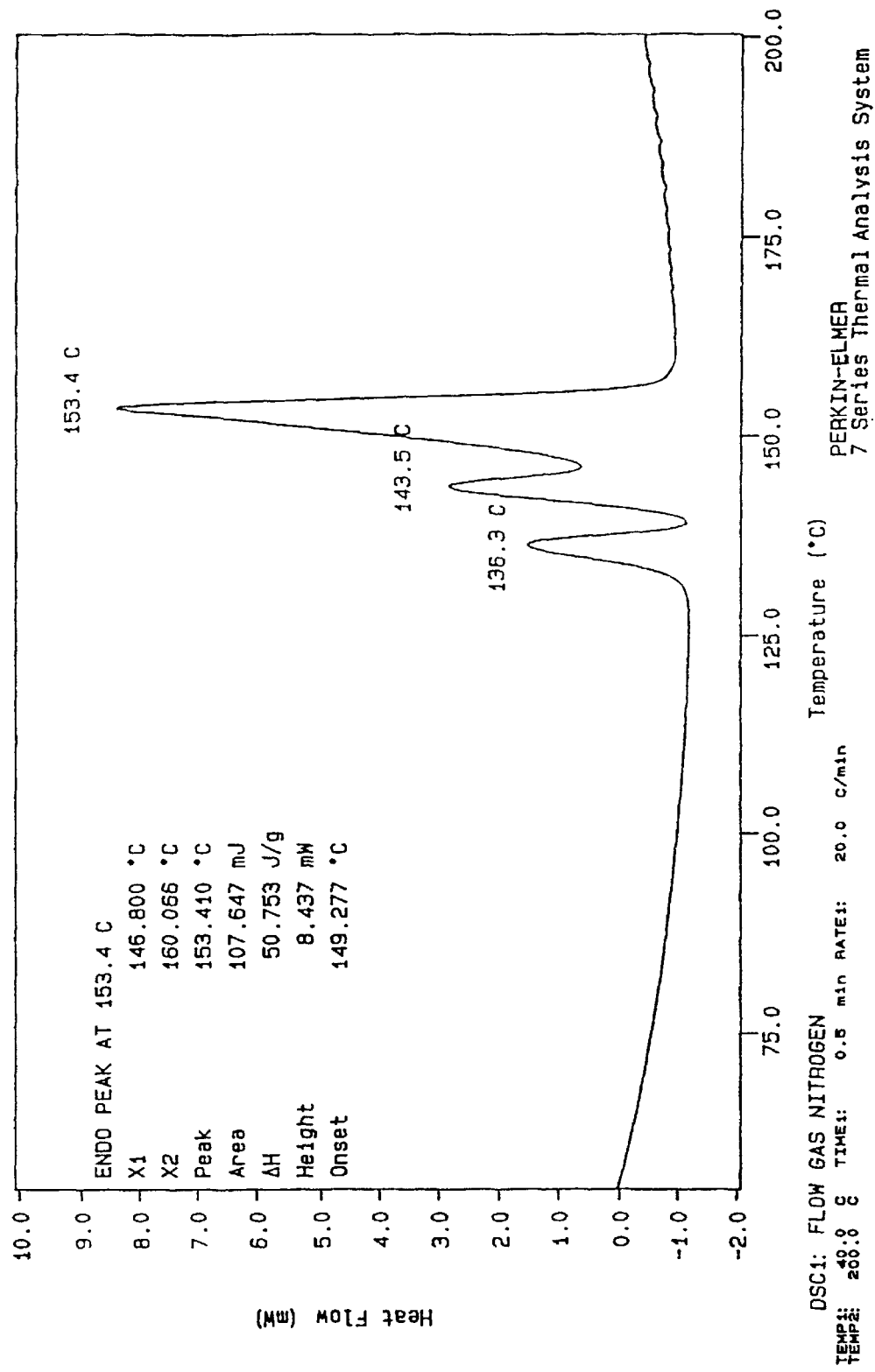

DSC thermogram for Reference Example 3

DSC thermogram for Reference Example 3A

DSC thermogram for Example 6

DSC thermogram for Example 7

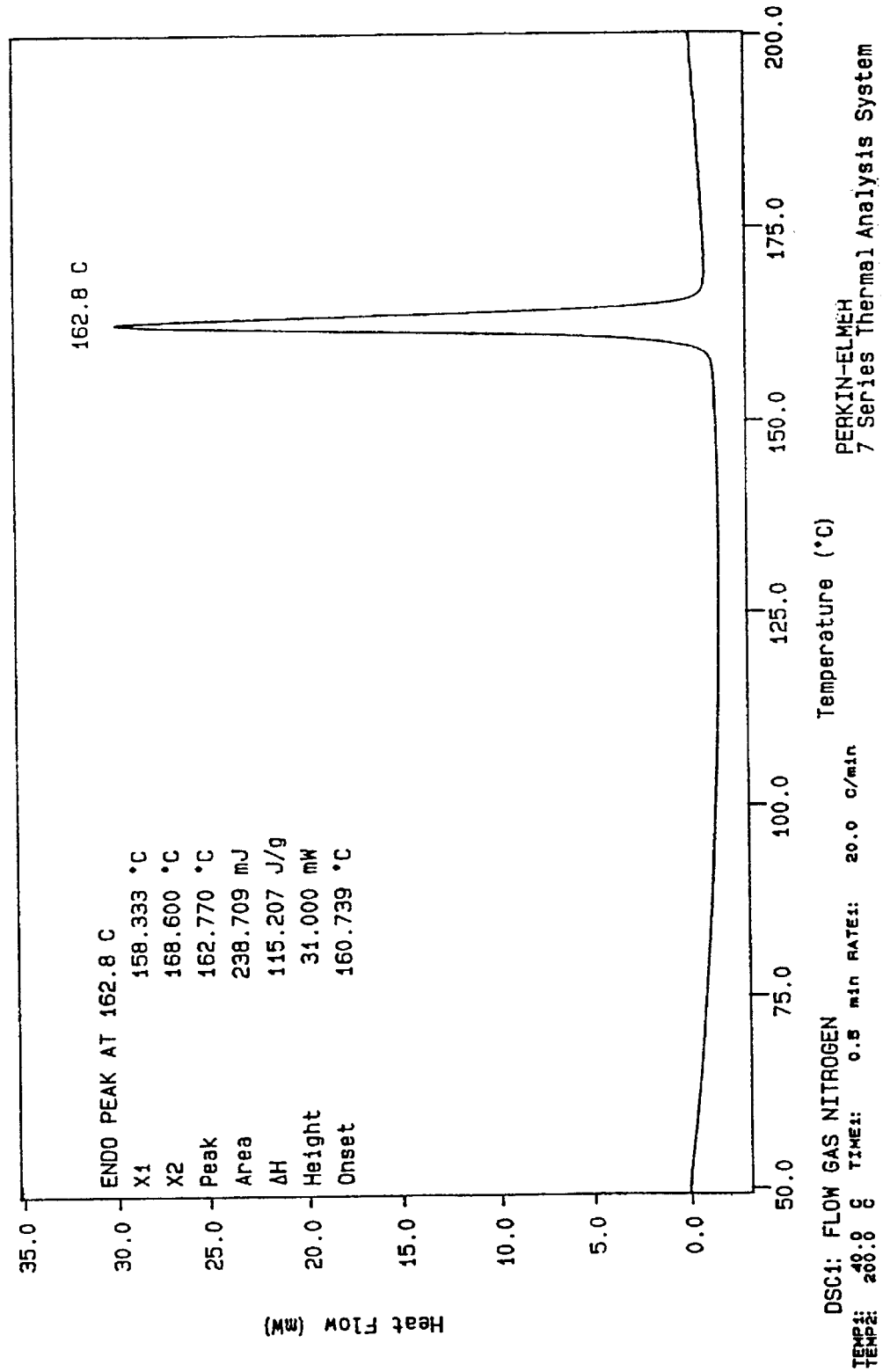

IR spectrum for dofetilide polymorph P162

IR spectrum for dofetilide polymorph P162a

IR spectrum for dofetilide polymorph P162b

IR spectrum for dofetilide polymorph P143

IR spectrum for Reference Example 1

IR spectrum for Reference Example 2

IR spectrum for Reference Example 3

DOFETILIDE POLYMORPHS

This application was filed under 35 U.S.C. §371 based on PCT/EP98/06641 which was filed Oct. 9, 1998 which claims priority from British application 9722662.5 filed on Oct. 27, 1997.

The present invention relates to polymorphs of the compound known as dofetilide. More particularly, the invention relates to the novel dofetilide polymorphs known as P162, P162a and P143, and to processes for the preparation of, compositions containing and to the uses of, such polymorphs. Dofetilide, N-[4-(2-[2-[4-(methanesulphonamido)phenoxy]-N'-methylethylamino]ethyl)phenyl]methanesulphonamide, has the following structure:

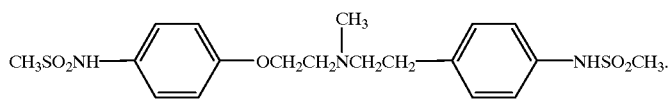

Dofetilide is disclosed in EP-A-0245997 as an antiarrhythmic agent that prolongs the duration of the action potential in cardiac muscle and conducting tissue, thereby increasing refractoriness to premature stimuli. It is therefore a Class III antiarrhythmic agent according to the classification of Vaughan Williams ("Anti-Arrhythmic Action", E. M. Vaughan Williams, Academic Press, 1980). It is effective in atria, ventricles and conducting tissue both in vitro and in vivo and could therefore be useful for the prevention and treatment of a wide variety of ventricular and supraventricular arrhythmias including atrial and ventricular fibrillation. Since it does not alter the speed at which impulses are conducted, it has less propensity than other antiarrhythmic drugs (mostly Class I) to precipitate or aggravate arrhythmias and it also produces less neurological side effects. It also lacks negative inotropic activity and therefore offers advantages over other antiarrhythmic agents in patients with impaired cardiac pump function.

The use of dofetilide in treating heart failure, particularly congestive heart failure, is described in European Patent Application no. 98306188.8, the teaching of which is incorporated herein by reference.

A capsule formulation of dofetilide is currently preferred. Dofetilide is a very potent drug and is therefore to be used in very low dosage. Since a very low drug loading will be required for the capsule formulation, it is essential that the active ingredient has a small particle size to ensure that a homogeneous blend is achieved.

The previously known methods of preparing dofetilide that are described in EP-A-0245997 are difficult to reproduce and have either produced a mixture of dofetilide polymorphs P162/P162a, P162b/P136 or P162b/P136/P143 or, essentially, dofetilide polymorph P136 or P162b, all of which tend to crystallise in an agglomerated form that would have to be deagglomerated (e.g. by milling or micronisation) to achieve the required small particle size. Hence, none of these products would be directly suitable for use in a capsule formulation.

It is an object of this invention to provide a suitable, substantially pure, crystalline, polymorphic form of dofetilide that can be easily, economically and reproducibly prepared with the required small particle size for use in a capsule formulation, preferably without any milling of the drug being necessary in the production process.

It has now been surprisingly found that this object has been achieved by the present invention which provides a substantially pure, crystalline, polymorphic form of dofetilide known as P162 and an inventive process for the preparation thereof. Dofetilide polymorph P162 crystallises from aqueous acetonitrile as flakes/plates with a consistently small particle size distribution, 90% of the particles being less than 45 $\mu$m in size. This form therefore does not require milling before use in a capsule formulation. It is also non-hygroscopic over a broad range of relative humidities, is chemically and physically stable, is rapidly absorbed in vivo and it can be routinely and reproducibly prepared in commercial quantities by the crystallisation process described herein.

Accordingly, the present invention provides substantially pure, crystalline, dofetilide polymorph P162 which is characterised by differential scanning calorimetry (DSC) in which it exhibits an endothermic thermal event at about 162° C.

Dofetilide polymorph P162 is further characterised by a powder X-ray diffraction (PXRD) pattern obtained by irradiation with copper K-alpha$_1$ X-rays (wavelength=1.5406 Angstroms) which shows main peaks with interplanar spacings at dÅ 21.303, 10.597, 7.053, 5.288, 5.088, 4.856, 4.793, 4.569, 4.504, 4.430, 4.256, 4.230, 4.133, 3.956, 3.911, 3.866, 3.674, 3.606, 3.524, 3.424, 3.384, 3.309, 3.255, 3.171, 3.083, 3.038, 3.021, 2.893, 2.842, 2.776, 2.679, 2.598, 2.557, 2.503, 2.482, 2.436, 2.419, 2.399, 2.345 and 2.323.

Dofetilide polymorph P162 is yet further characterised by an infrared (IR) spectrum as a mull in nujol which shows absorption bands at 3246, 3013, 2807, 2776, 1907, 1611, 1593, 1510, 1398,1366, 1357, 1321, 1300, 1277, 1251, 1220, 1171, 1146, 1106, 1091, 1051, 1031, 1023, 994, 966, 934, 925, 903, 851, 825, 808, 774, 723, 657, 603, 586, 559, 538, 528, 509, 499, 461 and 431 cm$^{-1}$.

Dofetilide polymorph P162 has been made available by the surprising finding that crystallisation of any other form of dofetilide from aqueous acetonitrile produces this polymorph as the product.

The present invention further provides the substantially pure, crystalline, dofetilide polymorphs P162a and P143. It will be appreciated that these polymorphs are not only to be regarded as synthetic intermediates that can be further processed to dofetilide polymorph P162 by crystallisation from aqueous acetonitrile, they also have the same therapeutic properties thereas. However, dofetilide polymorphs P162a and P143, and P162b and P136, are not as suitable as dofetilide polymorph P162 for use in preparing capsule formulations of the drug, principally because milling to achieve the required particle size is often required. Dofetilide polymorphs P162a and P162b have similar PXRD patterns and IR spectra, but different DSC characteristics, to dofetilide polymorph P162. The differences in the melting points of these polymorphs are due to varying degrees of disorder within the crystal structures of the polymorphs.

Substantially pure, crystalline, dofetilide polymorph P162a is characterised by DSC in which it exhibits an endothermic thermal event at about 160° C.

Dofetilide polymorph P162a is further characterised by a PXRD pattern obtained by irradiation with copper K-alpha$_1$ X-rays (wavelength=1.5406 Angstroms) which shows main peaks with interplanar spacings at dÅ 21.306, 10.603, 7.054, 5.289, 5.114, 5.094, 4.860, 4.572, 4.431, 4.260, 4.247, 4.228, 4.153, 4.136, 3.955, 3.870, 3.676, 3.607, 3.524, 3.435, 3.421, 3.384, 3.176, 3.038, 2.895, 2.778, 2.684, 2.559, 2.501, 2.486, 2.433, 2.326, 2.283, 2.248, 2.216, 2.171, 2.119, 2.051, 1.989 and 1.948.

Dofetilide polymorph P162a is yet further characterised by an IR spectrum as a mull in nujol which shows absorption bands at 3246, 3013, 2807, 2776, 1907, 1611, 1593,1510, 1397, 1366, 1357,1321, 1300, 1277, 1251, 1220, 1171, 1146, 1106, 1091, 1051, 1031, 1023, 994, 966, 934, 926, 903, 851, 825, 807, 774, 726, 657, 602, 586, 559, 538, 528, 509, 499, 461 and 430 cm$^{-1}$.

Substantially pure, crystalline, dofetilide polymorph P143 is characterised by DSC in which it exhibits an endothermic thermal event at about 144° C.

Dofetilide polymorph P143 is further characterised by a PXRD pattern obtained by irradiation with copper K-alpha$_1$ X-rays (wavelength=1.5406 Angstroms) which shows main peaks with interplanar spacings at dÅ 10.993, 9.006, 8.243, 6.769, 5.807, 5.530, 5.375, 5.104, 4.998, 4.735, 4.575, 4.539, 4.237, 4.179, 4.159, 4.019, 3.854, 3.705, 3.682, 3.601, 3.562, 3.482, 3.392, 3.343, 3.331, 3.263, 3.227, 3.173, 3.135, 3.082, 3.009, 2.946, 2.905, 2.859, 2.830, 2.803, 2.769, 2.672, 2.608 and 2.567.

Dofetilide polymorph P143 is yet further characterised by an IR spectrum as a mull in nujol which shows absorption bands at 3266, 3123, 3107, 3041, 3027, 3013, 2766,2723, 2610, 1895,1614, 1607,1587,1511, 1414,1395, 1337,1319, 1301,1287,1248, 1230,1215,1202,1187,1157,1148, 1130, 1110, 1060, 1042, 1018, 1005, 980, 975, 959, 940, 917, 853, 844, 831, 803, 785, 766, 752, 743, 718, 640, 613, 553, 536, 526, 509, 499, 455 and 429 cm$^{-1}$.

The expression "substantially pure" when used in conjunction with dofetilide polymorphs P162, P162a and P143 means at least 95% by weight pure. More preferably, "substantially pure" means at least 98% by weight pure and most preferably means at least 99% by weight pure.

Dofetilide polymorph P162 can be prepared by crystallisation of any other form of dofetilide, including polymorphic mixtures thereof, from aqueous acetonitrile. Preferably, from 98.5:1.5 to 99.5:0.5, by volume, acetonitrile:water is used as the crystallisation solvent. Most preferably, about 99:1, by volume, acetonitrile:water is used.

Dofetilide polymorph P162a can be prepared by dissolving any other form of dofetilide in an aqueous solution of a suitable base such as sodium hydroxide, adjusting the solution to about pH 8.5 using a suitable mineral acid, e.g. hydrochloric acid, and collecting the product. In this process, when sodium hydroxide and hydrochloric acid are used, sodium chloride may be co-precipitated as an impurity.

Dofetilide polymorph P143 can be prepared by dissolving any other form of dofetilide in methanol, applying the solution obtained to a silica column, eluting the column with methanol and concentrating the eluted solution to dryness under reduced pressure to provide a crystalline product.

Synthetic routes to prepare dofetilide are described in EP-A-0245997 and in the present Reference Examples section.

BRIEF DESCRIPTION OF THE DRAWINGS

FIG. 1–5, 5A, 6, 6A, 7, 7A, 7B, 7C, and 7D are PXRD patterns of certain dofetilide polymorphs or mixtures thereof.

FIG. 8–12, 12A, 13, 13A, 14, 14A, 14B, 14C and 14D are DSC thermographs of certain dofetilide polymorphs or mixtures thereof.

Figure 1:
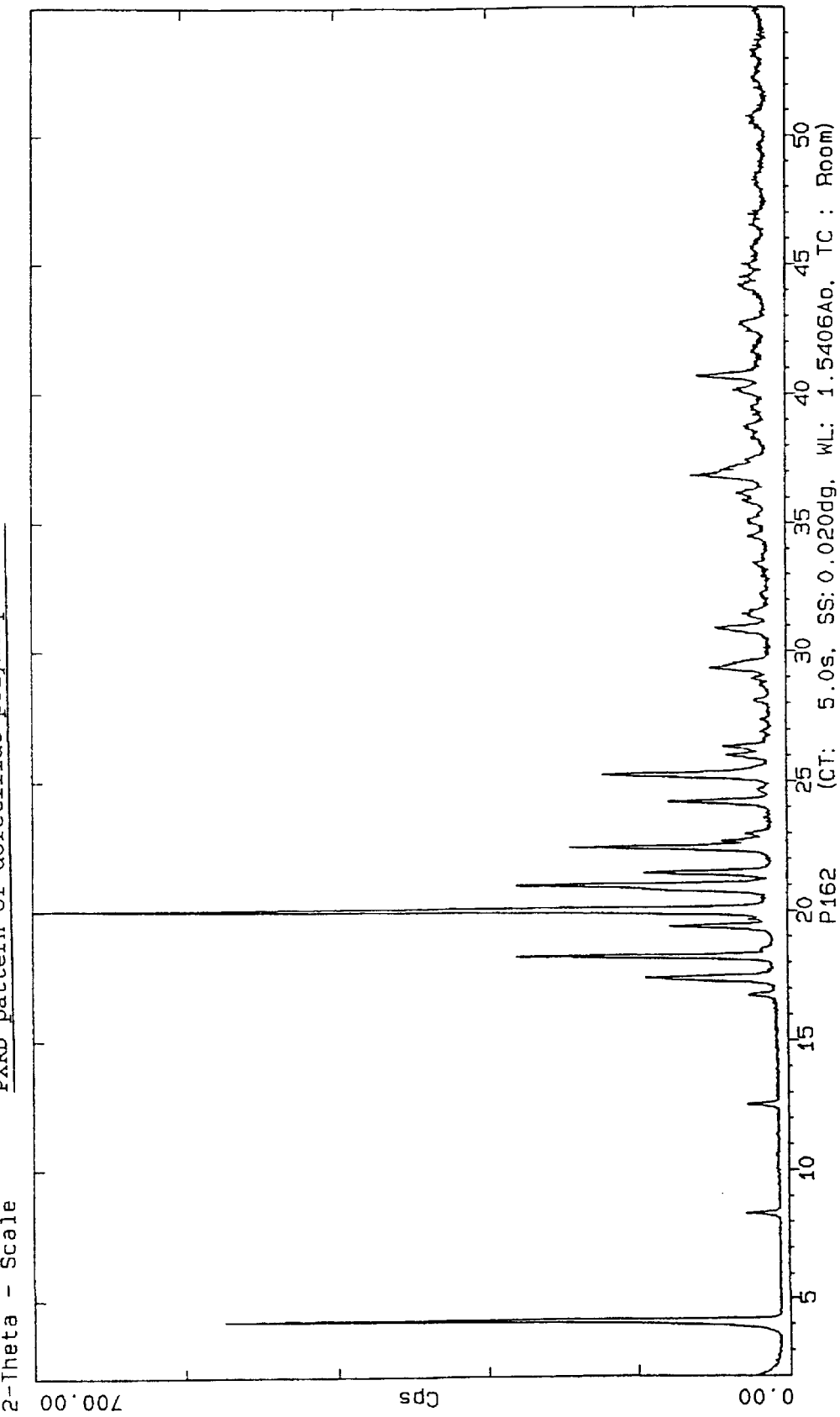

For assessment of the antiarrhythmic pharmacological effects of the dofetilide polymorphs, dog isolated cardiac tissue is used. Right ventricular trabeculae, papillary muscle or Purkinje fibres are isolated from either ventricle, mounted in an organ bath containing physiological salt solution and stimulated electrically. The resultant action potentials are recorded using intracellular microelectrodes. The effect of increasing the concentration of the polymorph within the bathing solution on the action potential duration and on the effective refractory period (ERP) are assessed. ERP is measured by stimulating the tissue with extra stimuli at progressively shorter inter-stimulus intervals until the extra stimulus fails to elicit an action potential. Essentially, the methods used are as described by Gwilt M., Arrowsmith J. E., Blackburn K. J. et al., "UK-68798. A novel, potent and highly selective class III antiarrhythmic agent which blocks potassium channels in cardiac cells", J. Pharmacol. Exp. Ther., 256, 318–24 (1991).

Methods for assessing the activity of the dofetilide polymorphs in treating heart failure are described in European Patent Application no. 98306188.8.

The dofetilide polymorphs can be administered alone but will generally be administered in admixture with a pharmaceutically acceptable diluent or carrier selected with regard to the intended route of administration and standard pharmaceutical practice. For example, they may be administered orally in the form of tablets containing such excipients as starch or lactose, or in capsules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other solutes, for example, enough salts or glucose to make the solution isotonic with blood.

The dofetilide polymorphs are preferably administered as capsule formulations. Such formulations may be prepared by mixing the dofetilide polymorph together with suitable carriers or excipients such as microcrystalline cellulose, dried maize starch, colloidal silicon dioxide and magnesium stearate.

For administration to man in the treatment of cardiac conditions such as ventricular and supraventricular arrhythmias, including atrial and ventricular fibrillation, it is expected that oral dosages of the compounds of the formula (I) will be in the range of from 0.125 to 1 mg, preferably from 0.25 to 1 mg, daily, taken in up to two divided doses per day, for an average adult patient (70 kg). Thus, for a typical adult patient, individual tablets or capsules might, for example, contain from 0.125 to 0.5 mg of active compound together with a suitable pharmaceutically acceptable diluent, excipient or carrier. Variations may occur depending on the weight and condition of the subject to be treated as will be known to medical practitioners.

Appropriate dosages of the dofetilide polymorphs for treating heart failure are described in European Patent Application no. 98306188.8. It will be appreciated that reference to medical treatment means curative, palliative or prophylactic treatment.

The invention therefore provides:
(i) substantially pure, crystalline, dofetilide polymorph P162, P162a or P143;
(ii) a process for the preparation of substantially pure, crystalline, dofetilide polymorph P162, P162a or P143;

(iii) a pharmaceutical composition comprising substantially pure, crystalline, dofetilide polymorph P162, P162a or P143, together with a pharmaceutically acceptable diluent or carrier;

(iv) a pharmaceutical capsule composition comprising substantially pure, crystalline, dofetilide polymorph P162, P162a or P143, together with a pharmaceutically acceptable diluent or carrier;

(v) substantially pure, crystalline, dofetilide polymorph P162, P162a or P143 for use as a medicament;

(vi) the use of substantially pure, crystalline, dofetilide polymorph P162, P162a or P143 for the manufacture of an antiarrhythmic agent;

(vii) a method of treating cardiac arrhythmia which comprises administering an effective amount of substantially pure, crystalline, dofetilide polymorph P162, P162a or P143, or a pharmaceutically acceptable composition thereof, to an animal, including a human being, in need of such treatment;

(viii) the use of substantially pure, crystalline, dofetilide polymorph P162, P162a or P143 for the manufacture of a medicament for treating heart failure, particularly congestive heart failure; and (ix) a method of treating heart failure, particularly congestive heart failure, which comprises administering an effective amount of substantially pure, crystalline, dofetilide polymorph P162, P162a or P143, or a pharmaceutically acceptable composition thereof, to an animal, including a human being, in need of such treatment.

EXAMPLES 1–8

The following Examples illustrate the preparation of the novel dofetilide polymorphs P162, P162a and P143, and the known dofetilide polymorph P162b. PXRD, IR, DSC and particle size analytical data for representative samples of these polymorphs are given in Tables 1 to 5.

EXAMPLE 1

Dofetilide Polymorph P162

To a stirred solution of acetonitrile (18 liters) and water (180 ml) was added dofetilide[1] (3.62 kg) and the mixture heated to achieve complete dissolution of the solid material.

1. The starting material may be pre-treated with charcoal to remove impurities before use using the following method.

To a stirred solution of acetonitrile (10,145 ml) and water (101 ml) was added dofetilide (2028.9 g) and the mixture heated to achieve complete dissolution of the solid material. Decolourising carbon (BDH [trade mark], 202.9 g) was added and the mixture heated under reflux for 15 minutes.

A pre-coated filter pad was prepared by suspending CLARCEL-FLO (trade mark) filter aid (200 g) in acetonitrile (1000 ml) and filtering the mixture with suction onto a paper membrane. The filtrate was discarded and the pad washed with acetonitrile (1000 ml) until the filtrate ran clear. The pad was sucked until firm but damp and the washings discarded. The hot dofetilide solution was filtered through the pad with suction and the filtrate cooled to ambient temperature with stirring. The suspension was granulated for 18 hours at ambient temperature. The solid was collected by filtration, washed with acetonitrile (2×200 ml) and the product dried under reduced pressure at 70° C. to provide 1525.6 9 of material.

The hot solution was filtered through a pad of CLARCEL-FLO (trade mark) filter aid (prepared as described in Footnote 1 below) and the pad was washed with acetonitrile. The filtrate was stirred and cooled to ambient temperature. The suspension was granulated for 18 hours at ambient temperature, the solid collected by filtration, washed with acetonitrile (2×400 ml) and the product dried under reduced pressure at 70° C. to provide the title compound (3.043 kg).

EXAMPLE 2

Dofetilide Polymorph P162a

Dofetilide (100 g) was dissolved with stirring in a solution of sodium hydroxide (25 g) in water (1000 ml). The solution was treated with decolourising carbon (5 g) for 30 minutes at ambient temperature and the carbon filtered off. The filtrate was adjusted to pH 8.5 with concentrated hydrochloric acid and the mixture granulated for 90 minutes. The solid was collected by filtration and washed with water (2×100 ml). The solid was dissolved in a solution of sodium hydroxide (25 g) in water (1000 ml) and the treatment with decolourising carbon repeated as before. The filtrate was adjusted to pH 8.5 as before and the mixture granulated for 90 minutes. The solid was filtered off, washed with water and dried under reduced pressure at 70° C. to give the title compound (93.3 g).

EXAMPLE 3

For Reference

Dofetilide Polymorph P162b

Dofetilide (37.0 g) was dissolved with stirring in acetone (750 ml) at ambient temperature and the solution clarified by filtration through a pad of CLARCEL-FLO (trade mark) filter aid. The filtrate was evaporated under reduced pressure ensuring that the temperature did not exceed 20° C. The resulting syrup crystallised and acetone (100 ml) was added. The solid was collected by filtration and dried under reduced pressure at 70° C. overnight to give the title compound (29.1 g).

EXAMPLE 4

For Reference

Dofetilide Polymorph P162b

Dofetilide is heated to about 5° C. above the melting point and then cooled to ambient temperature to provide a non-crystalline glass-like solid. This glass is then heated to from 70 to 125° C. to provide the title compound as a crystalline solid.

EXAMPLE 5

Dofetilide Polymorph P143

Dofetilide (60 g) was dissolved with stirring in methanol (6000 ml) and the resulting solution applied to a column of silica (WOELM Type TSC [trade mark]) (1000 g). The column was eluted with methanol and the initial 12 liters of the eluted solution was concentrated to dryness under reduced pressure to provide the title compound as a powder that was dried under reduced pressure at 60° C. (54.9 g).

EXAMPLE 6

Dofetilide Polymorph P162

Dofetilide polymorph P162a was crystallised from aqueous acetonitrile by a similar method to that used in Example 1 to provide dofetilide polymorph P162.

EXAMPLE 7

Dofetilide Polymorph P162

Dofetilide polymorph P162b was crystallised from aqueous acetonitrile by a similar method to that used in Example 1 to provide dofetilide polymorph P162.

EXAMPLE 8

Dofetilide Polymorph P162

Dofetilide polymorph P143 was crystallised from aqueous acetonitrile by a similar method to that used in Example 1 to provide dofetilide polymorph P162.

REFERENCE EXAMPLES 1, 1A, 2, 2A, 3, 3A and 4

In the following Reference Examples 1, 1A, 2, 2A, 3 and 3A, the crystallisation conditions of Examples 7,19, 20, 21 and 22 of EP-A-0245997 were repeated. The skilled person will appreciate that the synthetic routes used to prepare dofetilide in each of the Examples described in EP-A-0245997 will have no effect on the polymorph/polymorph mixture produced. It is solely the crystallisation conditions used that will determine this. The melting points were determined using an Electrothermal IA9100 apparatus in conjunction with a benzanilide reference standard.

PXRD, IR, DSC and particle size data for the products of these Reference Examples are given in Tables 1 to 5.

None of Reference Examples 1, 1A, 2, 2A, 3 and 3A provides substantially pure dofetilide polymorph P162, P162a or P143.

Reference Example 4 describes the preparation of dofetilide used as the starting material in Examples 1 to 5 and Reference Examples 1, 1A, 2, 2A, 3 and 3A.

REFERENCE EXAMPLE 1

Re. Examples 21 and 22 of EP-A-0245997

Dofetilide Polymorph P136/P162b Mixture

Dofetilide (5.0 g) was suspended in ethyl acetate (100 ml) and the stirred mixture heated to the reflux temperature. After 15 minutes under reflux, further ethyl acetate (100 ml) was added and after an additional 15 minutes, more ethyl acetate (100 ml) was added. The hot solution was filtered and cooled but no crystallisation occurred. The solution was heated under reflux, reduced to a volume of ca. 100 ml by evaporation of the solvent, cooled and allowed to stand at room temperature overnight. The crystalline product was collected by filtration, washed with cold ethyl acetate and dried (1.7 g). m.p. 160–1° C.*

* Benzanilide standard (Literature m.p. 163° C.) m.p. 164–5° C.

REFERENCE EXAMPLE 1A

Re. Examples 21 and 22 of EP-A-0245997

Dofetilide Polymorph P162/P162a Mixture

The lack of reproducibility of Examples 21 and 22 of EP-A-0245997 is demonstrated by the fact that on repeating the crystallisation conditions of Reference Example 1 using dofetilide (20.0 g), a mixture of dofetilide polymorphs P162/P162a was obtained.

REFERENCE EXAMPLE 2

Re. Examples 19 and 20 of EP-A-0245997

Dofetilide Polymorph P136/P162b Mixture

Dofetilide (5.0 g) was added to ethyl acetate (300 ml) and the mixture stirred and heated under reflux to achieve complete dissolution. The hot solution was filtered and the filtrate treated with n-hexane (100 ml). A white precipitate resulted and the suspension was granulated at room temperature overnight. The solid was collected by filtration, washed with n-hexane and dried (3.7 g). m.p. 158–60° C.*

* Benzanilide standard (Literature m.p. 163° C.) m.p. 164–5° C.

REFERENCE EXAMPLE 2A

Re. Examples 19 and 20 of EP-A-0245997

Dofetilide Polymorph P136/P162b/P143 mixture

The lack of reproducibility of Examples 19 and 20 of EP-A-0245997 is demonstrated by the fact that on repeating the crystallisation conditions of Reference Example 2 using dofetilide (20.0 g), a mixture of dofetilide polymorphs P1 36/P162b/P143 was obtained.

REFERENCE EXAMPLE 3

Re. Example 7 of EP-A-0245997

Dofetilide Polymorph P136

Dofetilide (10.0 g) was added to ethyl acetate (200 ml) and the mixture stirred and heated under reflux. The resulting suspension was treated with methanol, dropwise, until complete dissolution occurred. The hot solution was filtered and cooled but crystallisation did not occur. The solution was heated under reflux to evaporate the solvent until crystallisation commenced. The mixture was cooled, granulated for 4 hours, filtered and dried (2.6 g). m.p. 147–8° C*.

* Benzanilide standard (Literature m.p. 163° C.) m.p. 164–5° C.

REFERENCE EXAMPLE 3A

Re. Example 7 of EP-A-0245997

Dofetilide Polymorph P162b

The lack of reproducibility of Example 7 of EP-A-0245997 is demonstrated by the fact that on repeating the crystallisation conditions of Reference Example 3 using dofetilide (20.0 g), dofetilide polymorph P162b was obtained.

REFERENCE EXAMPLE 4

N-[4-(2-[2-[4-(Methanesulphonamido)phenoxy]-$N^1$-methylethylamino]ethyl)phenyl] methanesulphonamide (dofetilide)

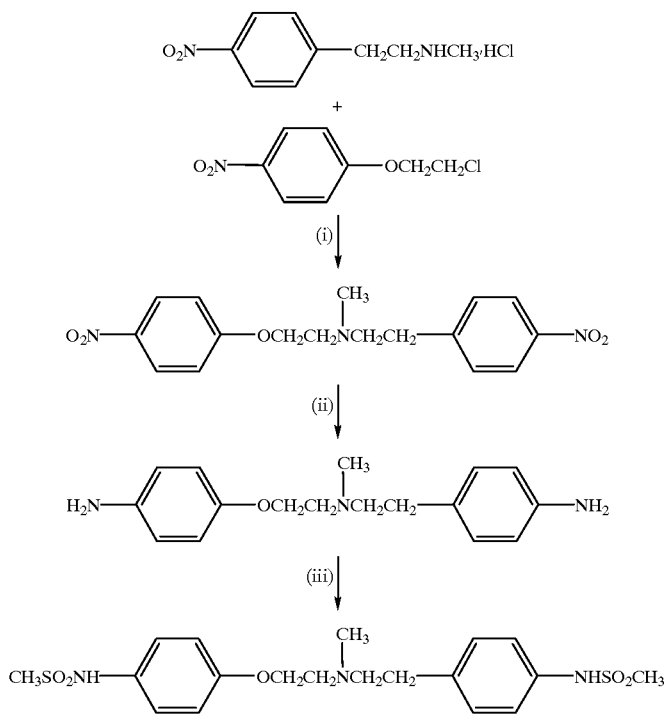

(i) N-Methyl-N-[2-(4-nitrophenoxy)ethyl]-4-nitrophenethylamine

To stirred de-ionised water (60 ml) was added N-methyl-2-(4-nitrophenyl)ethylamine hydrochloride[1] (20.0 g), 4-(2-chloroethoxy)nitrobenzene[2] (18.61 g), anhydrous potassium carbonate (14.04 g), potassium iodide (3.06 g) and tetra-n-butylammonium iodide (1.70 g). The mixture was heated under reflux for 3 hours, cooled to ca. 40° C., ethyl acetate (100 ml) added and stirred for 10 minutes. The organic phase was separated and the aqueous phase washed with ethyl acetate (2×100 ml). The combined organic phases were washed with water[3] (50 ml), concentrated under reduced pressure to a volume containing 2 ml per gram of the title compound (based on the theoretical yield) and then two volumes of ethanol added. The mixture was stirred and granulated at ambient temperature overnight, the solid collected by filtration, washed with ethanol (2×100 ml) and dried under reduced pressure at 40° C. to give the title compound (21.34 g, 67%).

1. J. Med. Chem., 33, 873–7 (1990). 2. J. Org. Chem., 49, 3114–21 (1984). 3. Brine may be used.

(ii) N-Methyl-N-[2-(4-aminophenoxy)ethyl]-4-aminophenethylamine

To methanol (2000 ml) was added the compound of part (i) (200 g) and 5% w/w palladium-on-carbon (containing 50% water) (20 g). The mixture was stirred and hydrogenated at 60 p.s.i. (414 kPa) until hydrogen uptake ceased. The catalyst was filtered off, washed with methanol (2×100 ml) and the combined filtrate and washings evaporated to low volume under reduced pressure. The residual solvents were replaced with toluene by azeotropic distillation and on completion of this process the volume of the solution was adjusted to ca. 400 ml with toluene (ca. 800 ml of toluene was used in total). The solution was cooled to ambient temperature and granulated for ca. 90 minutes. The solid was collected by filtration, washed with toluene (100 ml) and dried under reduced pressure at 40° C. to yield the title compound (152.3 g, 93%).

(iii) N-[4-(2-[2-[4-(Methanesulphonamido)phenoxy]-N[1]-methylethylamino]ethyl)phenyl]methanesulphonamide (dofetilide)

To stirred acetonitrile (235 ml) was added the compound of part (ii) (57.0 g), followed by triethylamine (50.5 g). To this mixture was slowly added a solution of methanesulphonyl chloride (57.2 g) in acetonitrile (50 ml) over 30 minutes[1]. The mixture was stirred for 90 minutes and quenched with water (200 ml). Sodium carbonate (26.7 g) was added and the mixture stirred for 20 minutes. The reaction mixture was reduced to half-volume by distillation[2], water (200 ml) added and distilled to half-volume again. The mixture was cooled, sodium hydroxide pellets (16.0 g) added and the mixture stirred for 3 hours at ambient temperature[3]. Concentrated hydrochloric acid (35 ml) was added, dropwise, over 30 minutes and the mixture granulated for 90 minutes.

The solid was collected by filtration, washed with water (2×70 ml) and dried under reduced pressure at 60° C. to provide the title compound[4] (87.4 g, 99%).

1. The temperature of the reaction mixture was not allowed to rise above 50° C during the addition. 2. This may also be achieved by evaporation under reduced pressure. 3. It should be ensured that the mixture has a pH>13 after this period. If not, further base should be added to achieve this pH. 4. HPLC indicated this material to be >99% pure. It can be further purified by carbon treatment (see Example 1, Footnote 1).

ANALYTICAL DATA a) PXRD

The powder X-ray diffraction patterns were determined using a Siemens D5000 powder X-ray diffractometer fitted with an automatic sample changer, a theta-theta goniometer, automatic beam divergence slits, a secondary monochromator and a scintillation counter.

The samples were prepared for analysis by packing the powder into 12 mm diameter, 0.25 mm deep cavities that had been cut into silicon wafer specimen mounts. Each specimen was rotated whilst being irradiated with copper K-alpha$_1$ X-rays (wavelength=1.5406 Angstroms) with the X-ray tube operated at 40 kV/40 mA. The analyses were performed with the goniometer running in step-scan mode set for a 5 second count per 0.02° step over a two-theta range of 2° to 55°.

FIG. 1 shows the PXRD pattern of dofetilide polymorph P162.

Figure 2:
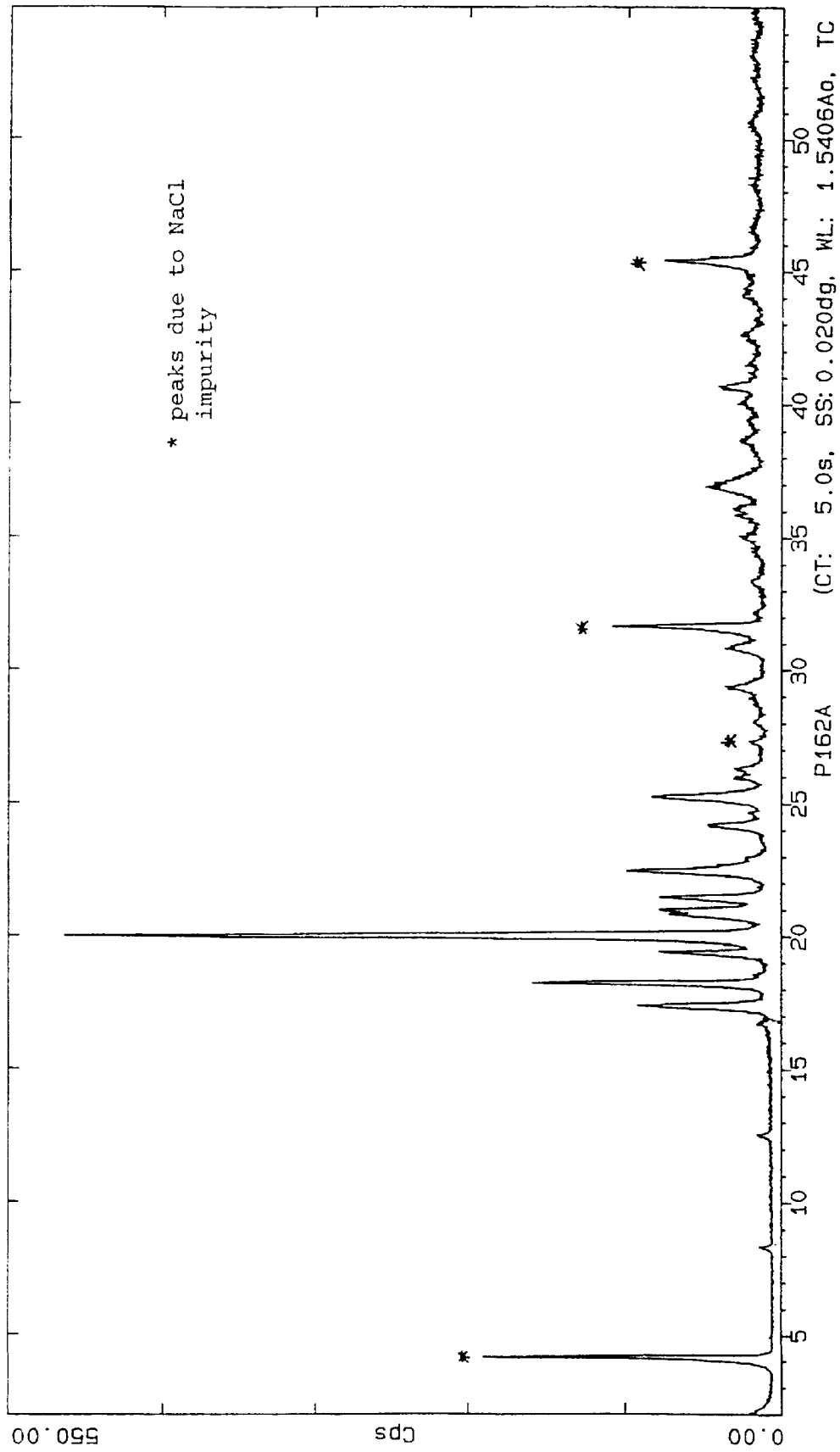

FIG. 2 shows the PXRD pattern of dofetilide polymorph P162a.

Figure 3:
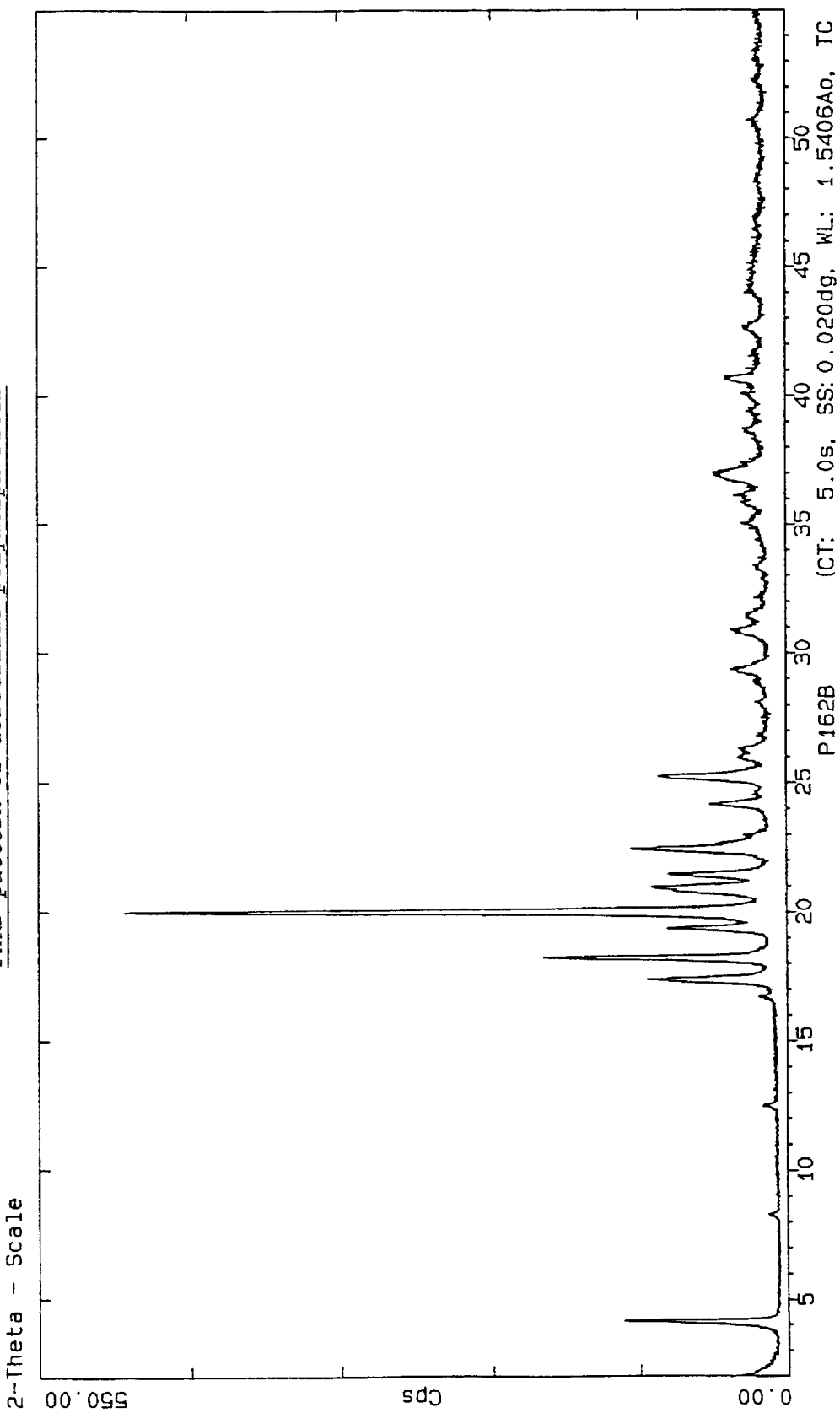

FIG. 3 shows the PXRD pattern of dofetilide polymorph P162b.

Figure 4:
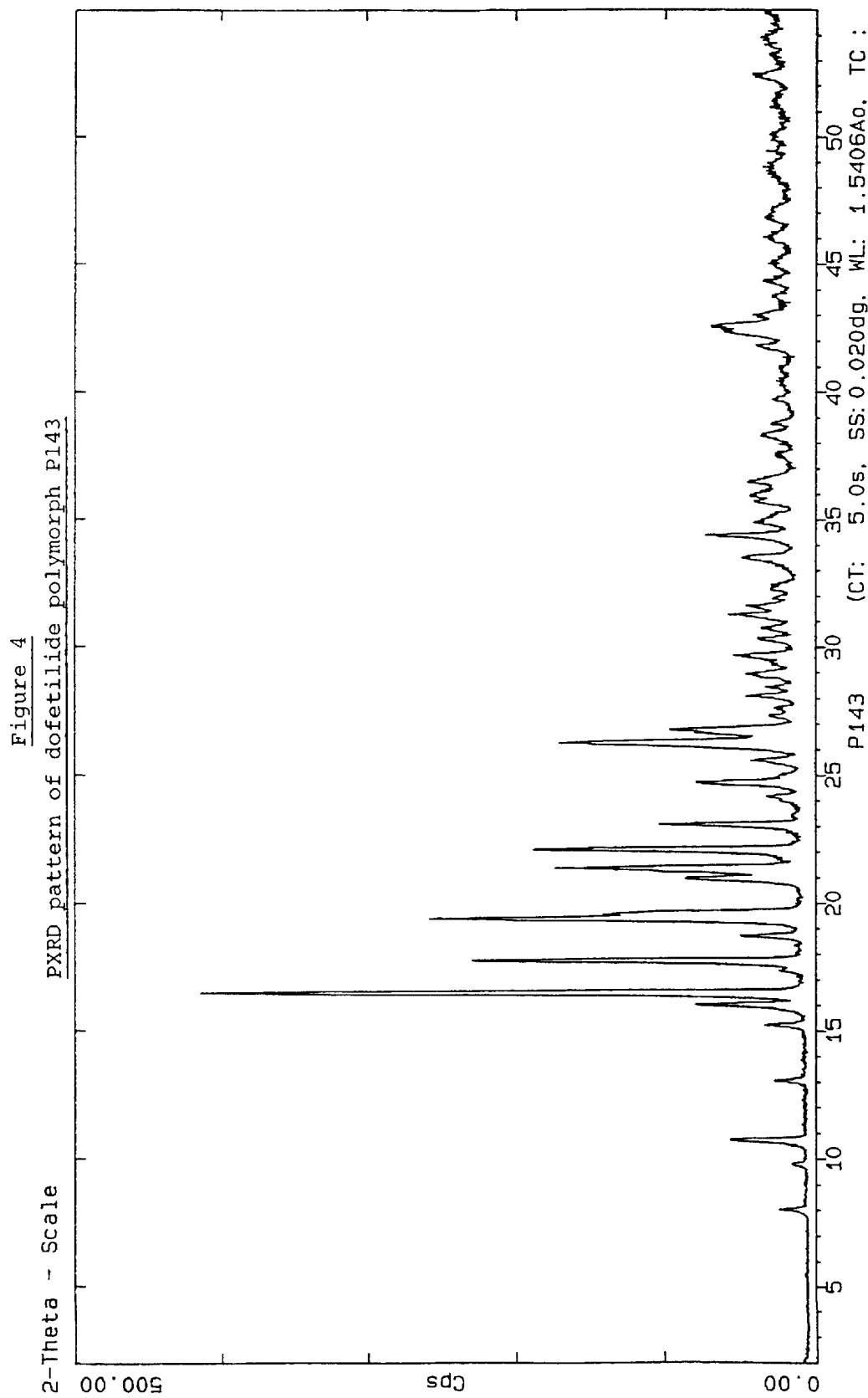

FIG. 4 shows the PXRD pattern of dofetilide polymorph P143.

Figure 5:
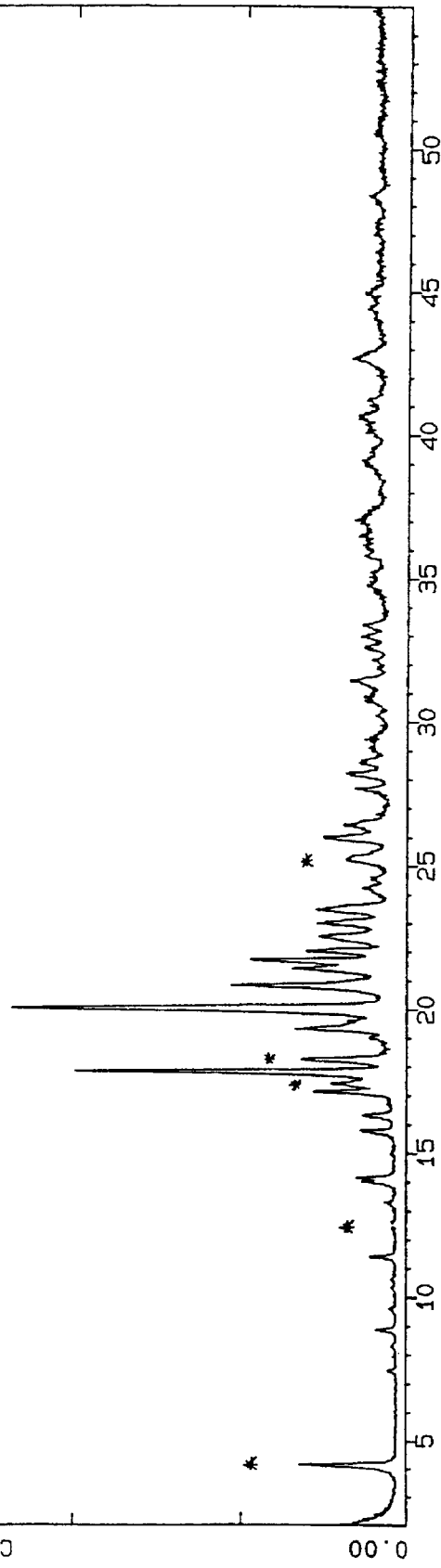

FIG. 5 shows the PXRD pattern of the product of Reference Example 1.

Figure 5A:
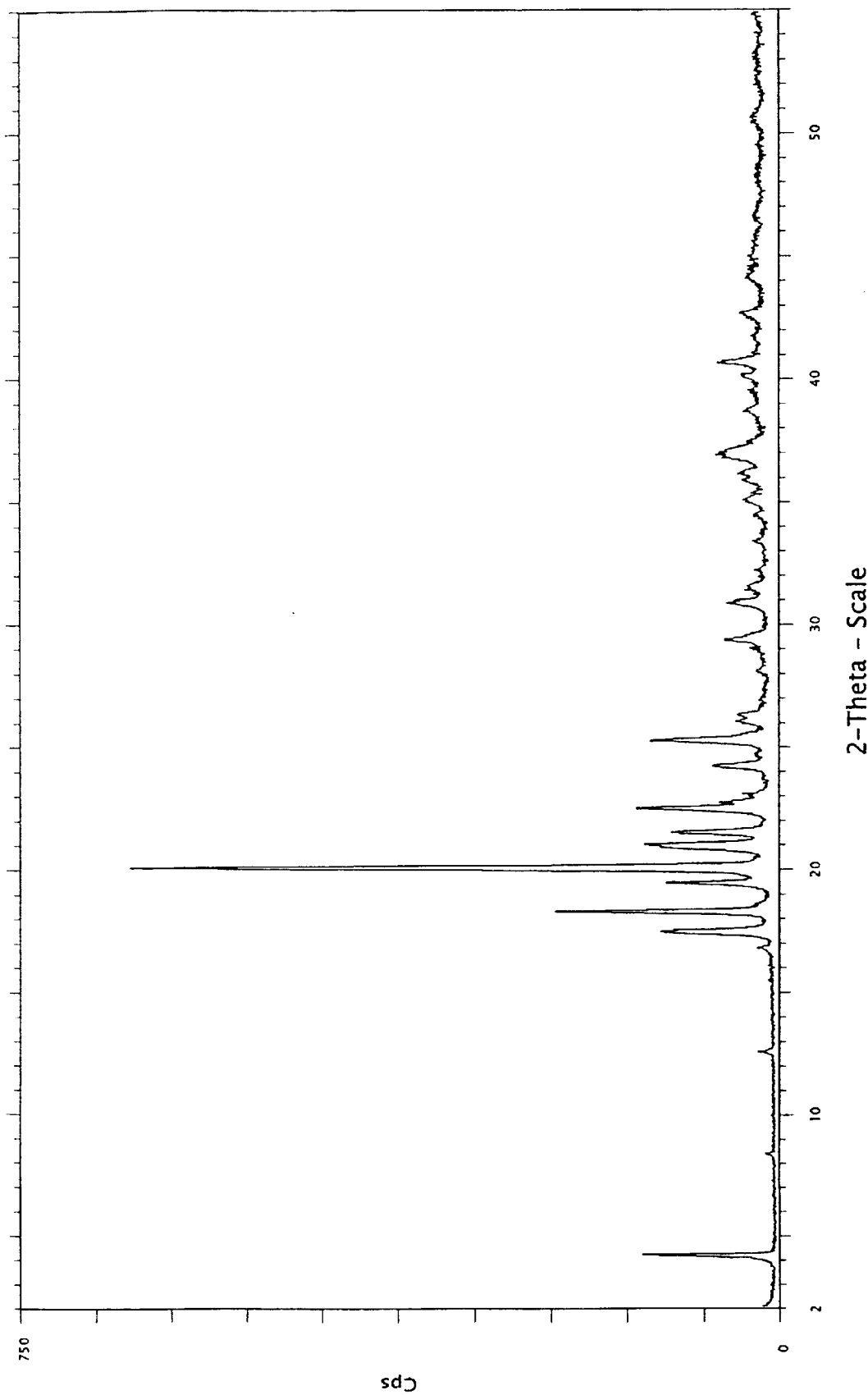

FIG. 5A shows the PXRD pattern of the product of Reference Example 1A.

Figure 6:
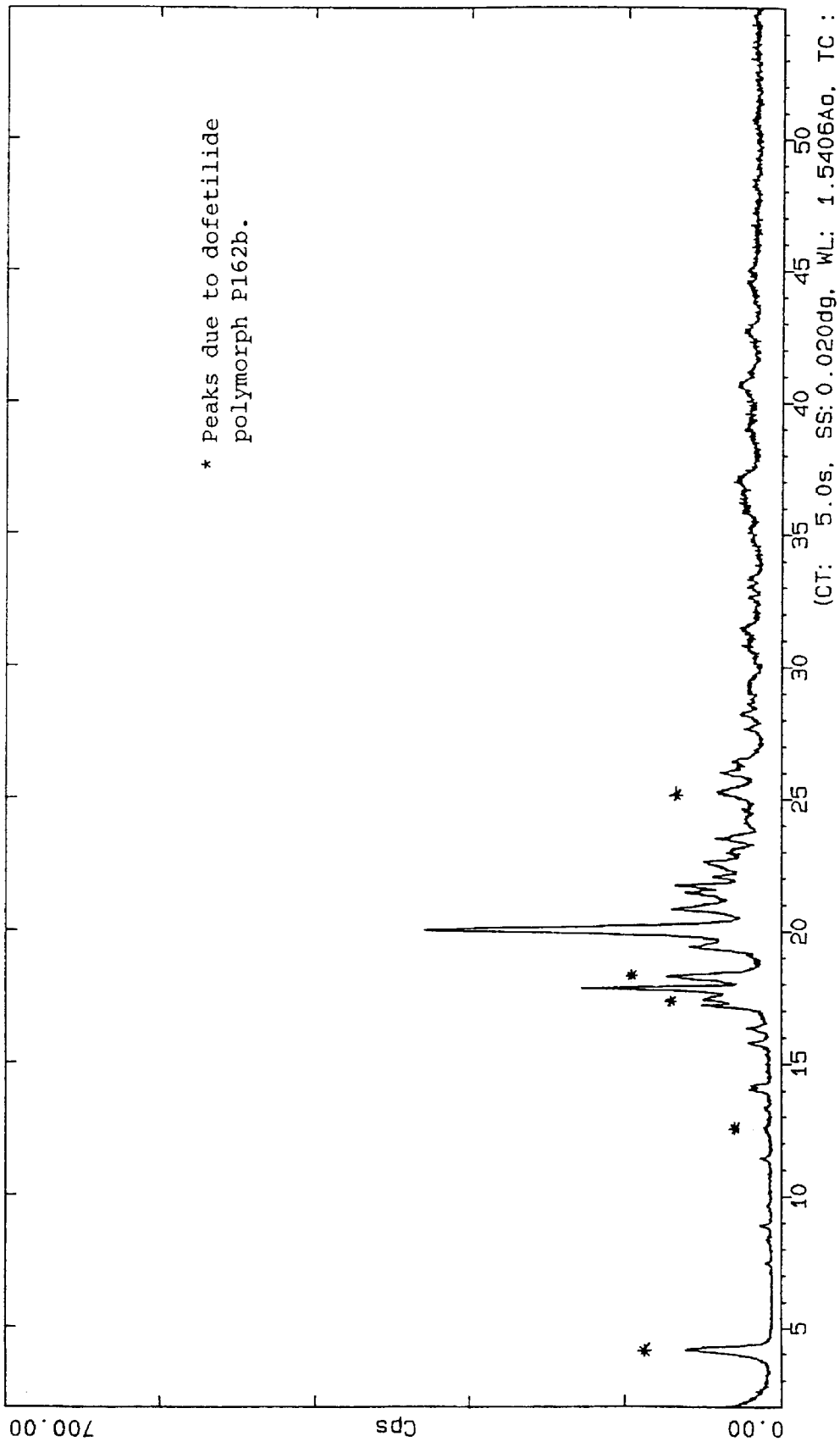

FIG. 6 shows the PXRD pattern of the product of Reference Example 2.

FIG. 6A shows the PXRD pattern of the product of Reference Example 2A.

Figure 7:
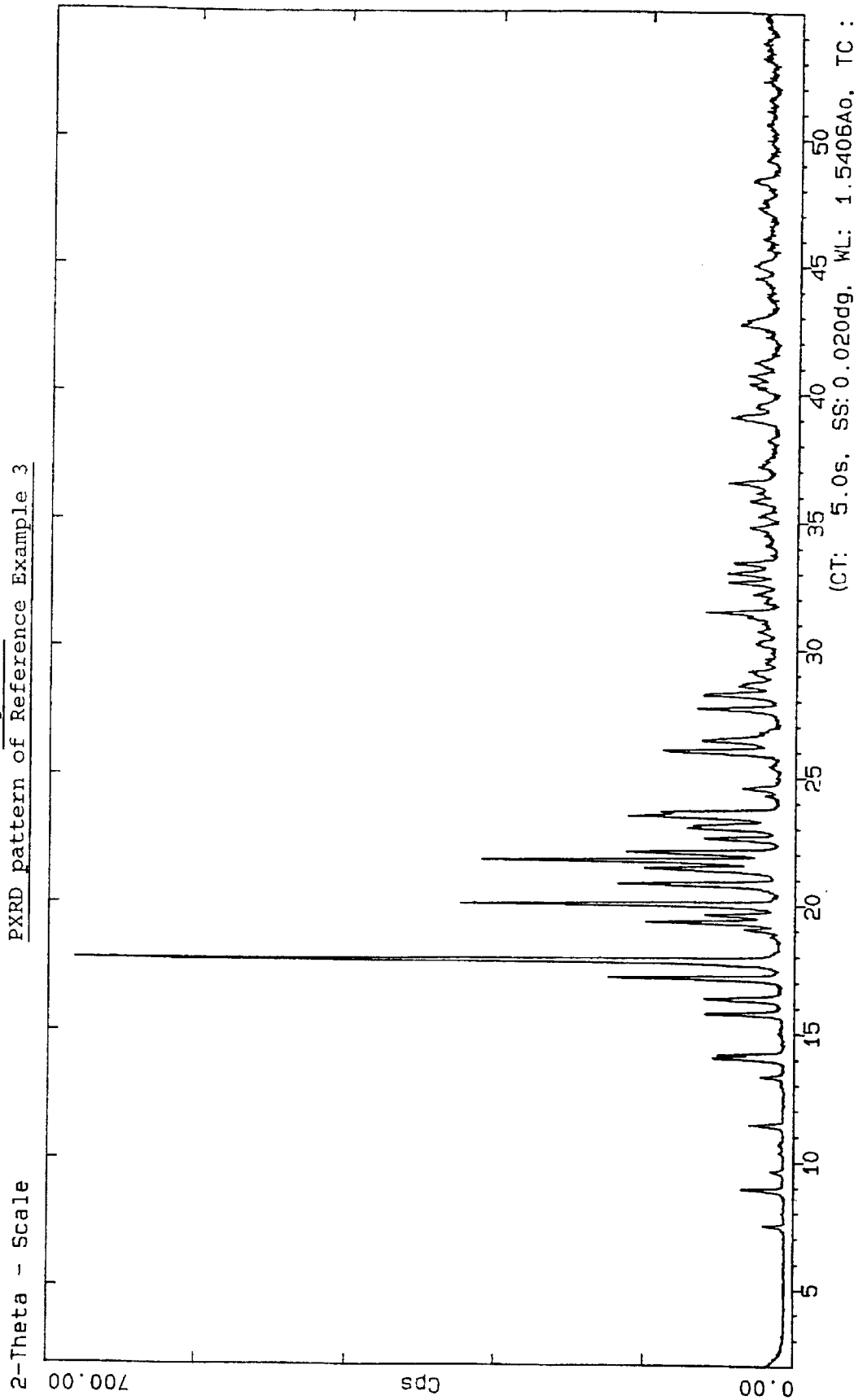

FIG. 7 shows the PXRD pattern of the product of Reference Example 3.

Figure 7A:
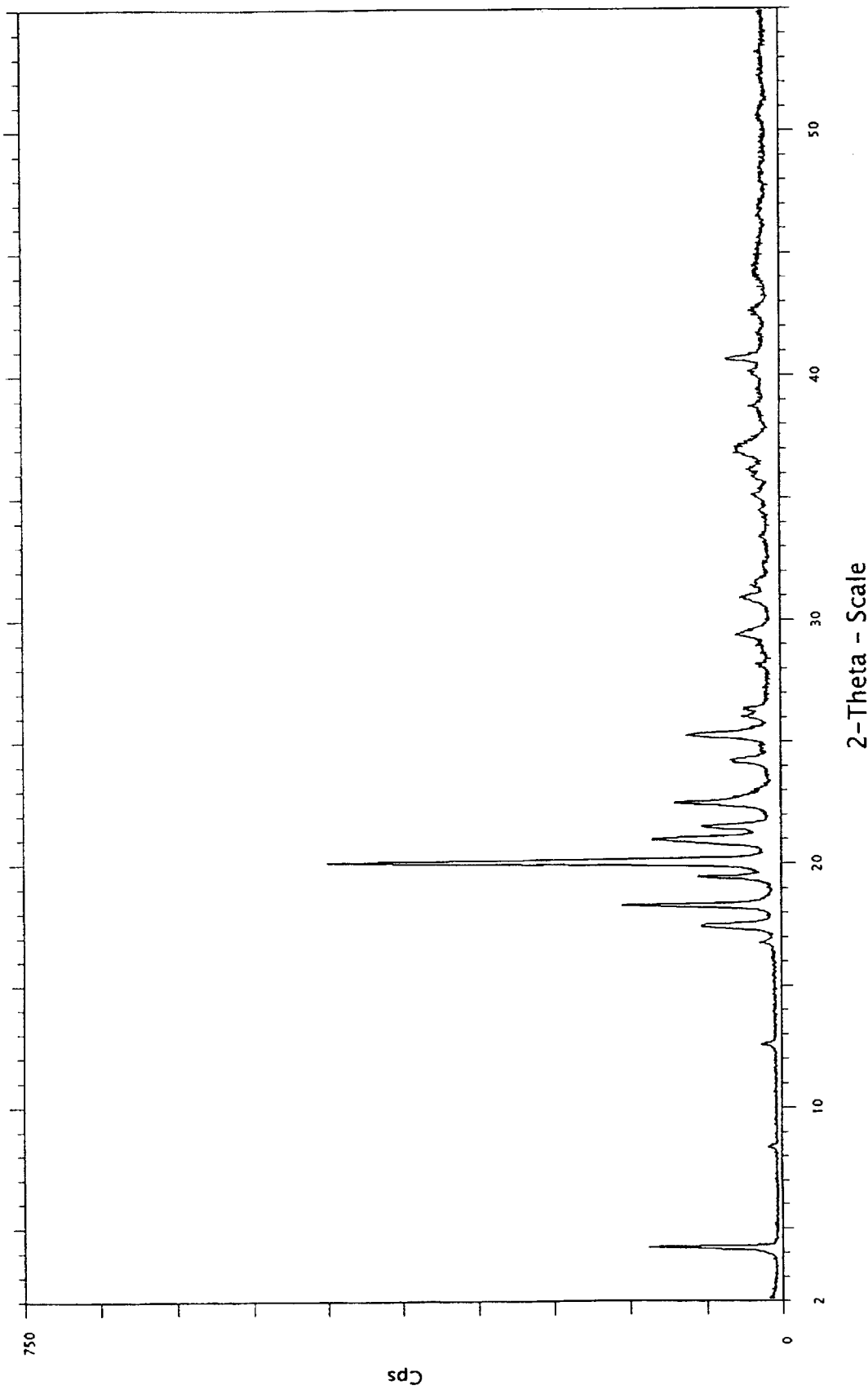

FIG. 7A shows the PXRD pattern of the product of Reference Example 3A.

FIG. 7B shows the PXRD pattern of the product of Example 6.

Figure 7C:
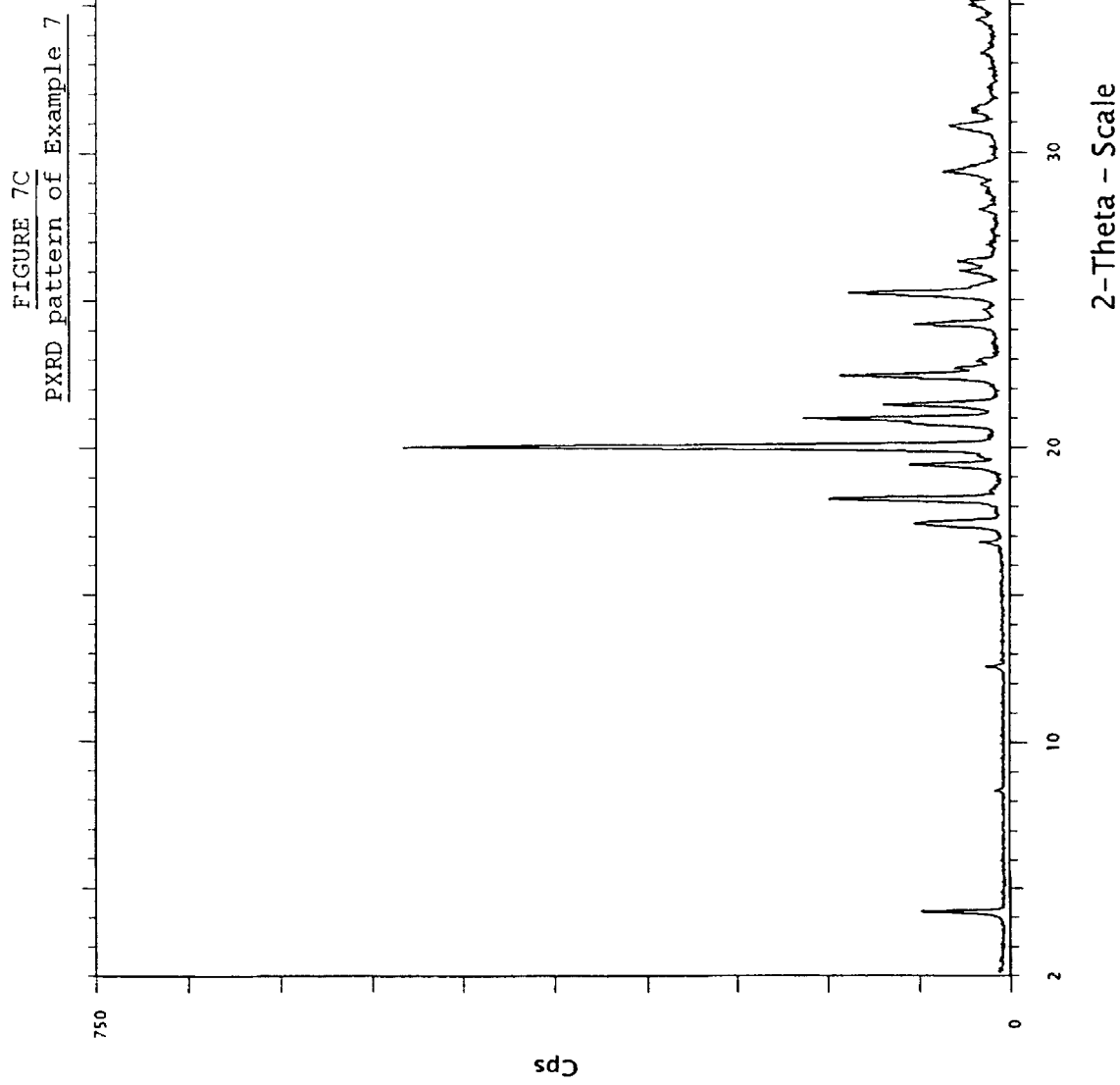

FIG. 7C shows the PXRD pattern of the product of Example 7.

Figure 7D:
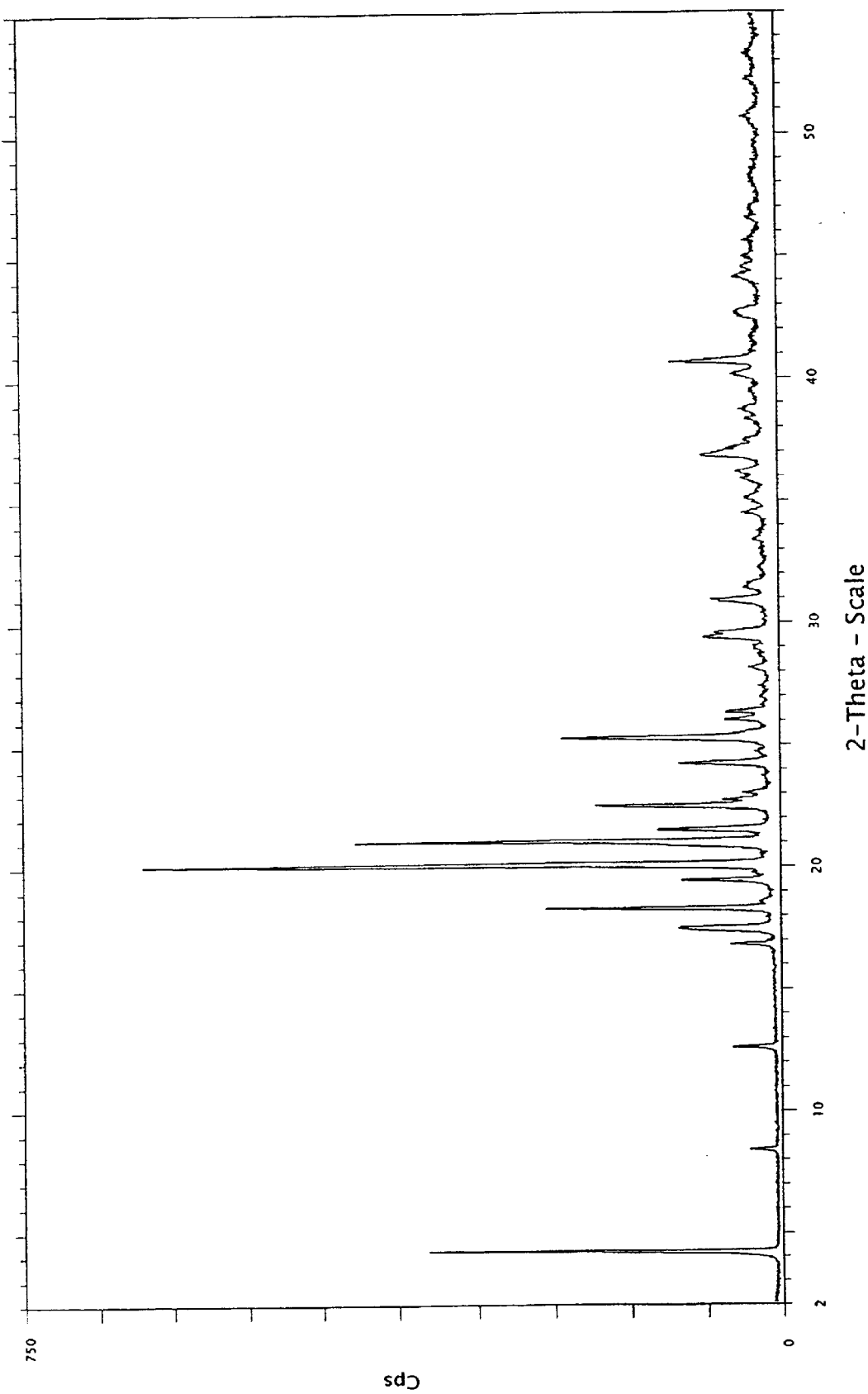

FIG. 7D shows the PXRD pattern of the product of Example 8.

The peak listings for the above Figures are given in Table 1 in which dÅ is a measurement of the interplanar spacing and $I/I_i$ is a measurement of the relative intensity.

TABLE 1

| P162 | | P162a[1] | | P162b | | P143 | |
|---|---|---|---|---|---|---|---|
| dÅ | $I/I_i$ | dÅ | $I/I_i$ | dÅ | $I/I_i$ | dÅ | $I/I_i$ |
| 21.303 | 74 | 21.306 | 40 | 21.508 | 24 | 10.993 | 5 |
| 10.597 | 5 | 10.603 | 2 | 10.640 | 2 | 9.006 | 3 |
| 7.053 | 4 | 7.054 | 2 | 7.073 | 3 | 8.243 | 12 |
| 5.288 | 4 | 5.289 | 2 | 5.292 | 3 | 6.769 | 5 |
| 5.088 | 18 | 5.114 | 16 | 5.098 | 20 | 5.807 | 7 |
| 4.856 | 36 | 5.094 | 19 | 4.868 | 37 | 5.530 | 18 |
| 4.793 | 3 | 4.860 | 34 | 4.580 | 17 | 5.375 | 100 |
| 4.569 | 15 | 4.572 | 16 | 4.436 | 100 | 5.104 | 5 |
| 4.504 | 3 | 4.431 | 100 | 4.270 | 16 | 4.998 | 54 |
| 4.430 | 100 | 4.260 | 15 | 4.250 | 17 | 4.735 | 11 |
| 4.256 | 17 | 4.247 | 14 | 4.234 | 20 | 4.575 | 62 |
| 4.230 | 36 | 4.228 | 16 | 4.140 | 17 | 4.539 | 33 |
| 4.133 | 18 | 4.153 | 11 | 3.961 | 23 | 4.237 | 20 |
| 3.956 | 28 | 4.136 | 16 | 3.921 | 9 | 4.179 | 25 |
| 3.911 | 8 | 3.955 | 20 | 3.679 | 11 | 4.159 | 41 |
| 3.866 | 5 | 3.870 | 4 | 3.528 | 19 | 4.019 | 45 |
| 3.674 | 15 | 3.676 | 9 | 3.426 | 6 | 3.854 | 24 |
| 3.606 | 3 | 3.607 | 4 | 3.388 | 6 | 3.705 | 4 |
| 3.524 | 24 | 3.524 | 17 | 3.172 | 4 | 3.682 | 7 |
| 3.424 | 7 | 3.435 | 5 | 3.090 | 4 | 3.601 | 18 |
| 3.384 | 8 | 3.421 | 6 | 3.040 | 8 | 3.562 | 5 |
| 3.309 | 3 | 3.384 | 6 | 2.895 | 7 | 3.482 | 9 |
| 3.255 | 2 | 3.176 | 3 | 2.842 | 5 | 3.392 | 40 |
| 3.171 | 3 | 3.038 | 6 | 2.782 | 4 | 3.343 | 18 |
| 3.083 | 4 | 2.895 | 7 | 2.684 | 3 | 3.331 | 22 |
| 3.038 | 9 | 2.778 | 3 | 2.559 | 6 | 3.263 | 6 |
| 3.021 | 6 | 2.684 | 3 | 2.504 | 5 | 3.227 | 5 |
| 2.893 | 8 | 2.559 | 5 | 2.492 | 6 | 3.173 | 10 |
| 2.842 | 5 | 2.501 | 6 | 2.482 | 7 | 3.135 | 7 |
| 2.776 | 2 | 2.486 | 6 | 2.431 | 10 | 3.082 | 10 |
| 2.679 | 3 | 2.433 | 10 | 2.326 | 5 | 3.009 | 12 |
| 2.598 | 4 | 2.326 | 5 | 2.283 | 5 | 2.946 | 8 |
| 2.557 | 4 | 2.283 | 4 | 2.250 | 5 | 2.905 | 8 |
| 2.503 | 5 | 2.248 | 5 | 2.216 | 8 | 2.859 | 13 |
| 2.482 | 6 | 2.216 | 8 | 2.164 | 4 | 2.830 | 9 |
| 2.436 | 12 | 2.171 | 4 | 2.119 | 5 | 2.803 | 6 |
| 2.419 | 7 | 2.119 | 5 | 2.047 | 5 | 2.769 | 6 |
| 2.399 | 4 | 2.051 | 5 | 1.798 | 5 | 2.672 | 11 |
| 2.345 | 3 | 1.989 | 7 | 1.748 | 3 | 2.608 | 17 |
| 2.323 | 5 | 1.948 | 3 | — | — | 2.567 | 9 |

TABLE 1-continued

| Reference Example 1[2] | | Reference Example 2[3] | | Reference Example 3[4] | |
|---|---|---|---|---|---|
| dÅ | $I/I_i$ | dÅ | $I/I_i$ | dÅ | $I/I_i$ |
| 21.243 | 26 | 21.252 | 25 | 11.793 | 3 |
| 11.808 | 3 | 12.384 | 1 | 11.028 | 1 |
| 10.606 | 2 | 11.815 | 2 | 9.911 | 6 |
| 9.937 | 6 | 10.567 | 2 | 9.183 | 2 |
| 9.207 | 2 | 9.925 | 4 | 8.513 | 1 |
| 8.540 | 2 | 9.135 | 2 | 8.262 | 1 |
| 8.317 | 2 | 7.721 | 4 | 7.715 | 5 |
| 7.755 | 8 | 7.042 | 2 | 6.638 | 4 |
| 7.049 | 2 | 6.633 | 2 | 6.280 | 9 |
| 6.658 | 4 | 6.300 | 7 | 6.237 | 10 |
| 6.309 | 10 | 6.229 | 7 | 5.874 | 1 |
| 6.243 | 10 | 5.603 | 7 | 5.610 | 11 |
| 5.624 | 10 | 5.418 | 8 | 5.411 | 12 |
| 5.428 | 9 | 5.147 | 21 | 5.159 | 25 |
| 5.170 | 22 | 5.078 | 20 | 4.968 | 100 |
| 5.081 | 18 | 4.966 | 55 | 4.653 | 6 |
| 4.977 | 84 | 4.850 | 31 | 4.586 | 20 |
| 4.857 | 26 | 4.569 | 24 | 4.516 | 12 |
| 4.662 | 8 | 4.546 | 19 | 4.426 | 46 |
| 4.583 | 26 | 4.426 | 100 | 4.263 | 24 |
| 4.518 | 13 | 4.255 | 29 | 4.144 | 19 |
| 4.432 | 100 | 4.137 | 26 | 4.082 | 43 |
| 4.263 | 44 | 4.088 | 28 | 4.025 | 23 |
| 4.145 | 28 | 4.027 | 18 | 3.924 | 12 |
| 4.093 | 39 | 3.969 | 14 | 3.857 | 13 |
| 4.031 | 24 | 3.936 | 19 | 3.835 | 10 |
| 3.966 | 15 | 3.859 | 13 | 3.783 | 22 |
| 3.943 | 21 | 3.840 | 12 | 3.760 | 16 |
| 3.858 | 19 | 3.779 | 17 | 3.655 | 3 |
| 3.782 | 22 | 3.670 | 8 | 3.614 | 6 |
| 3.670 | 10 | 3.617 | 9 | 3.495 | 3 |
| 3.628 | 7 | 3.520 | 16 | 3.420 | 18 |
| 3.612 | 7 | 3.422 | 16 | 3.363 | 12 |
| 3.522 | 14 | 3.368 | 12 | 3.317 | 3 |
| 3.425 | 20 | 3.311 | 6 | 3.216 | 13 |
| 3.370 | 15 | 3.217 | 9 | 3.155 | 12 |
| 3.222 | 11 | 3.158 | 10 | 3.113 | 7 |
| 3.164 | 13 | 3.116 | 7 | 3.063 | 5 |
| 3.123 | 10 | 3.048 | 8 | 3.022 | 3 |
| 3.109 | 10 | 2.901 | 9 | 2.950 | 5 |

Footnotes
1. Peaks due to any sodium chloride impurity have been omitted.
2. Dofetilide polymorph P136/P162b mixture.
3. Dofetilide polymorph P136/P162b mixture.
4. Dofetilide polymorph P136.

| Reference Example 1A[5] | | Reference Example 2A[6] | | Reference Example 3A[7] | |
|---|---|---|---|---|---|
| dÅ | $I/I_i$ | dÅ | $I/I_i$ | dÅ | $I/I_i$ |
| 21.415 | 20 | 21.514 | 15 | 21.346 | 29 |
| 10.615 | 2 | 9.939 | 3 | 10.617 | 2 |
| 7.054 | 3 | 8.302 | 3 | 7.064 | 4 |
| 5.286 | 3 | 7.755 | 3 | 5.295 | 4 |
| 5.087 | 18 | 7.039 | 3 | 5.093 | 17 |
| 4.859 | 34 | 6.819 | 3 | 4.857 | 34 |
| 4.775 | 4 | 6.299 | 6 | 4.573 | 18 |
| 4.571 | 17 | 5.865 | 4 | 4.431 | 100 |
| 4.430 | 100 | 5.607 | 5 | 4.237 | 28 |
| 4.237 | 20 | 5.409 | 23 | 4.137 | 17 |
| 4.135 | 16 | 5.163 | 13 | 3.956 | 23 |
| 3.958 | 22 | 5.080 | 22 | 3.867 | 5 |
| 3.907 | 7 | 5.025 | 28 | 3.676 | 11 |
| 3.861 | 4 | 4.975 | 40 | 3.602 | 4 |
| 3.675 | 10 | 4.852 | 34 | 3.524 | 20 |

TABLE 1-continued

| dÅ | I/I$_i$ | dÅ | I/I$_i$ | dÅ | I/I$_i$ |
|---|---|---|---|---|---|
| 3.607 | 4 | 4.749 | 9 | 3.423 | 8 |
| 3.524 | 19 | 4.577 | 26 | 3.384 | 7 |
| 3.420 | 6 | 4.548 | 28 | 3.173 | 5 |
| 3.386 | 6 | 4.429 | 100 | 3.088 | 6 |
| 3.309 | 3 | 4.259 | 31 | 3.038 | 9 |
| 3.175 | 3 | 4.214 | 25 | 2.892 | 8 |
| 3.076 | 5 | 4.156 | 24 | 2.850 | 6 |
| 3.039 | 8 | 4.141 | 27 | 2.778 | 3 |
| 2.895 | 8 | 4.097 | 26 | 2.682 | 4 |
| 2.848 | 5 | 4.031 | 22 | 2.599 | 4 |
| 2.836 | 5 | 3.866 | 17 | 2.555 | 5 |
| 2.777 | 4 | 3.782 | 14 | 2.503 | 6 |
| 2.682 | 4 | 3.687 | 11 | 2.483 | 7 |
| 2.599 | 4 | 3.521 | 20 | 2.433 | 9 |
| 2.556 | 5 | 3.417 | 16 | 2.322 | 6 |
| 2.500 | 5 | 3.340 | 11 | 2.245 | 6 |
| 2.481 | 8 | 3.229 | 8 | 2.216 | 11 |
| 2.431 | 9 | 3.161 | 9 | 2.163 | 5 |
| 2.398 | 5 | 3.018 | 10 | 2.118 | 6 |
| 2.324 | 5 | 2.9i0 | 10 | 2.052 | 5 |
| 2.277 | 4 | 2.899 | 10 | — | — |
| 2.245 | 6 | 2.844 | 11 | — | — |
| 2.215 | 9 | 2.744 | 8 | — | — |
| 2.161 | 4 | 2.714 | 7 | — | — |
| 2.116 | 6 | 2.681 | 10 | — | — |
| 3.038 | 12 | 2.896 | 10 | 3.041 | 12 |
| 3.019 | 8 | 2.849 | 6 | 3.023 | 9 |
| 2.894 | 11 | 2.778 | 3 | 2.893 | 9 |
| 2.847 | 6 | 2.684 | 4 | 2.847 | 5 |
| 2.777 | 3 | 2.601 | 5 | 2.828 | 5 |
| 2.679 | 4 | 2.559 | 6 | 2.775 | 3 |
| 2.602 | 5 | 2.508 | 6 | 2.682 | 4 |
| 2.559 | 5 | 2.486 | 7 | 2.556 | 4 |
| 2.504 | 6 | 2.439 | 13 | 2.503 | 5 |
| 2.482 | 7 | 2.419 | 8 | 2.482 | 6 |
| 2.438 | 13 | 2.400 | 5 | 2.437 | 12 |
| 2.416 | 9 | 2.346 | 5 | 2.398 | 5 |
| 2.398 | 5 | 2.328 | 6 | 2.347 | 5 |
| 2.346 | 5 | 2.284 | 5 | 2.323 | 5 |
| 2.325 | 7 | 2.247 | 7 | 2.280 | 4 |
| 2.287 | 4 | 2.218 | 13 | 2.244 | 7 |

Footnotes
5. Dofetilide polymorph P162/P162a mixture
6. Dofetilide polymorph P136/P162b/P143 mixture
7. Dofetilide polymorph P162b

| P162 EXAMPLE 6 | | P162 EXAMPLE 7 | | P162 EXAMPLE 8 | |
|---|---|---|---|---|---|
| dÅ | I/I$_i$ | dÅ | I/I$_i$ | dÅ | I/I$_i$ |
| 21.318 | 76 | 21.547 | 14 | 21.422 | 51 |
| 10.580 | 6 | 10.630 | 2 | 10.622 | 5 |
| 7.042 | 6 | 7.067 | 3 | 7.054 | 7 |
| 5.282 | 7 | 5.300 | 5 | 5.291 | 8 |
| 5.095 | 16 | 5.104 | 15 | 5.091 | 6 |
| 4.861 | 33 | 4.871 | 29 | 4.856 | 37 |
| 4.790 | 4 | 4.798 | 3 | 4.782 | 3 |
| 4.574 | 15 | 4.438 | 100 | 4.568 | 15 |
| 4.501 | 5 | 4.279 | 15 | 4.505 | 5 |
| 4.429 | 100 | 4.237 | 34 | 4.429 | 100 |
| 4.224 | 52 | 4.143 | 20 | 4.230 | 66 |
| 4.137 | 19 | 3.964 | 28 | 4.132 | 19 |
| 3.956 | 28 | 3.921 | 9 | 3.956 | 29 |
| 3.907 | 8 | 3.876 | 5 | 3.907 | 9 |
| 3.870 | 6 | 3.678 | 15 | 3.866 | 6 |
| 3.672 | 16 | 3.611 | 4 | 3.673 | 16 |
| 3.607 | 4 | 3.530 | 26 | 3.606 | 4 |
| 3.524 | 28 | 3.431 | 8 | 3.523 | 34 |
| 3.425 | 10 | 3.391 | 8 | 3.422 | 8 |
| 3.386 | 9 | 3.315 | 3 | 3.382 | 8 |
| 3.307 | 3 | 3.264 | 3 | 3.307 | 3 |
| 3.252 | 3 | 3.178 | 5 | 3.256 | 3 |
| 3.172 | 5 | 3.087 | 4 | 3.172 | 5 |
| 3.083 | 5 | 3.043 | 11 | 3.083 | 4 | b) DSC

Differential scanning calorimetry (DSC) was performed using a Perkin Elmer DSC-7 machine fitted with an automatic sample changer. Approximately 2 mg of each sample was accurately weighed into a 50 microliter aluminium pan and crimp-sealed with a perforated lid.

The samples were heated at 20° C./minute over the range 40° C. to 200° C. with a nitrogen gas purge.

Figure 8:
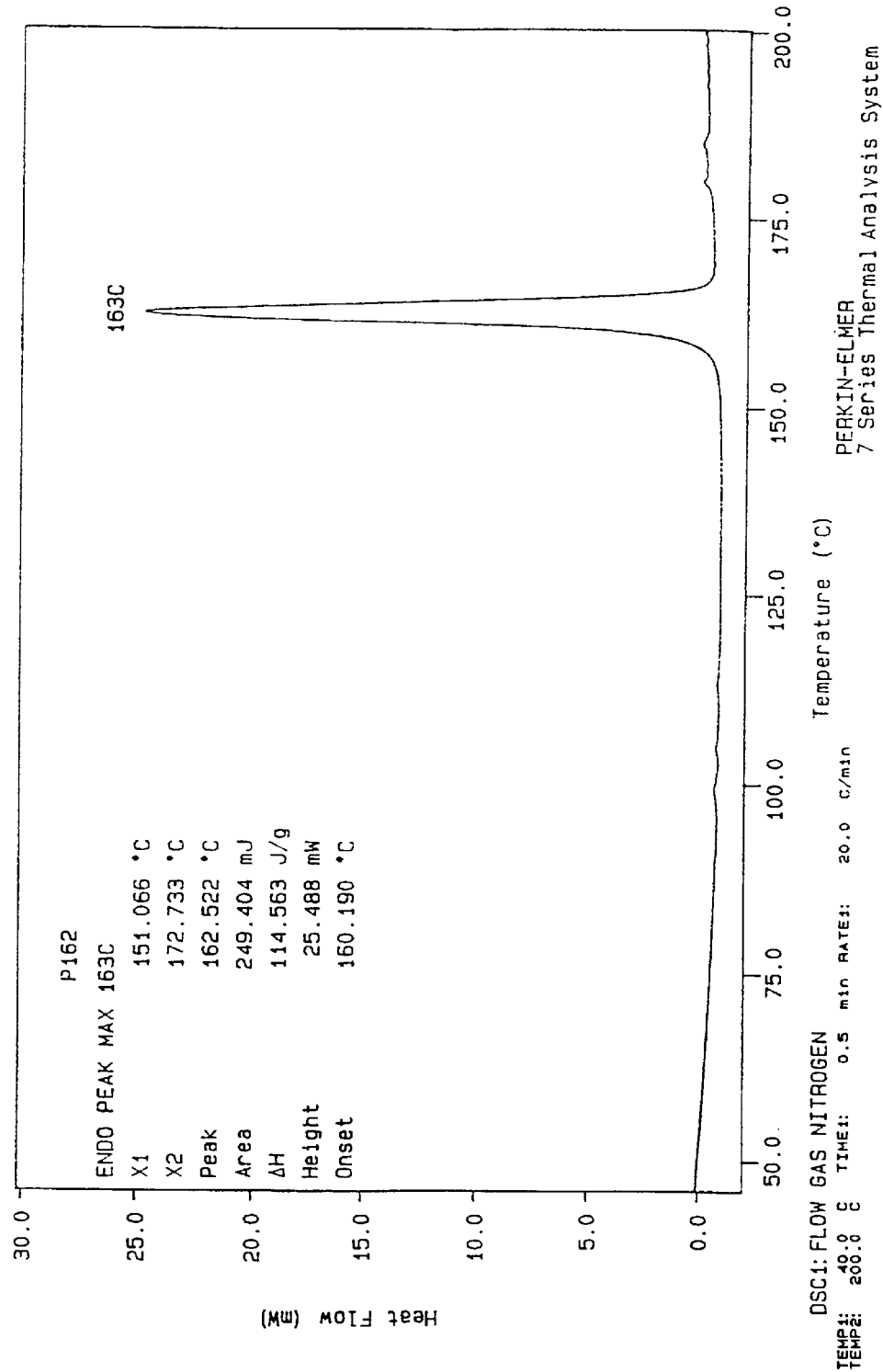

FIG. 8 shows the DSC thermogram for dofetilide polymorph P162.

Figure 9:
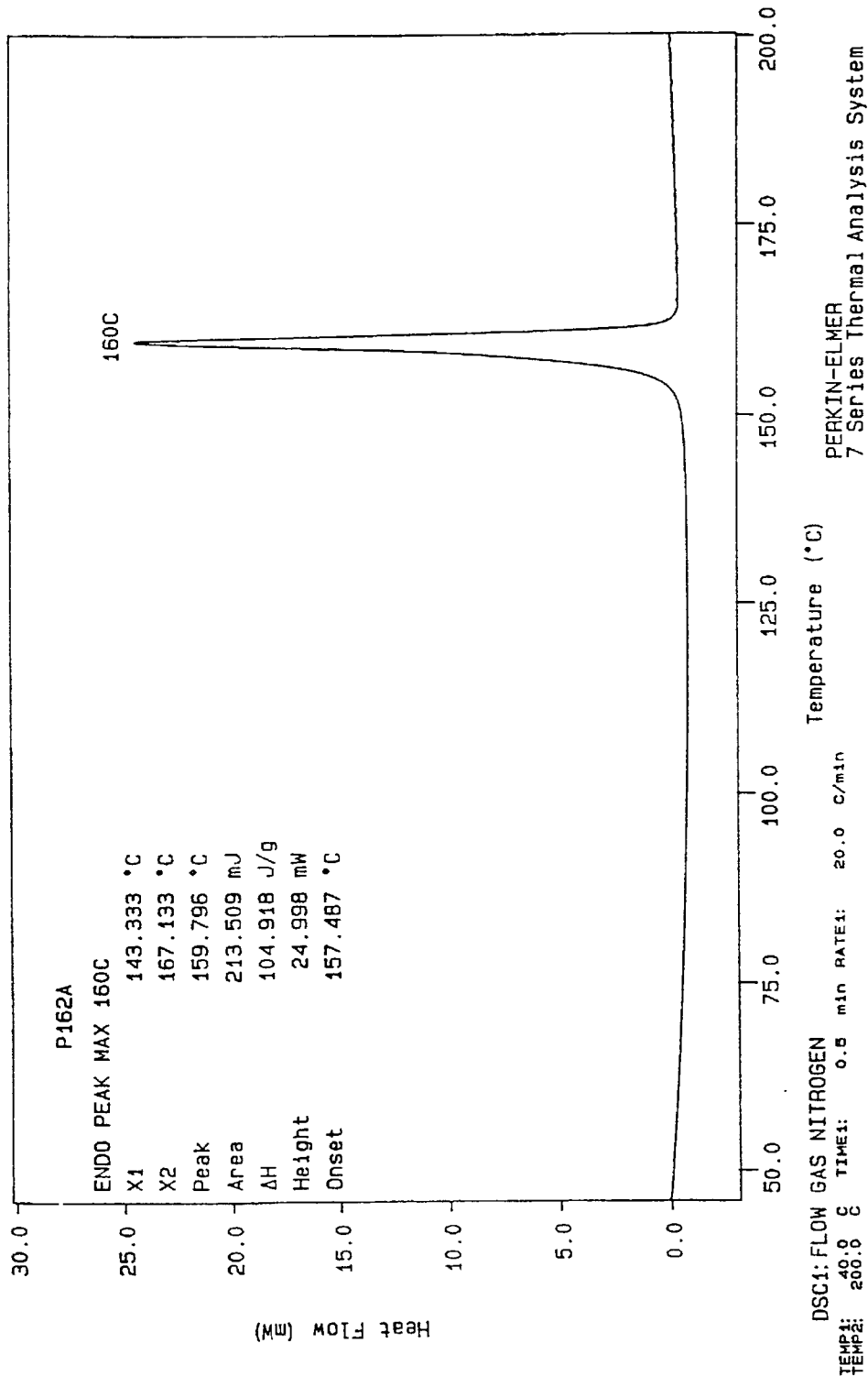

FIG. 9 shows the DSC thermogram for dofetilide polymorph P162a.

Figure 10:
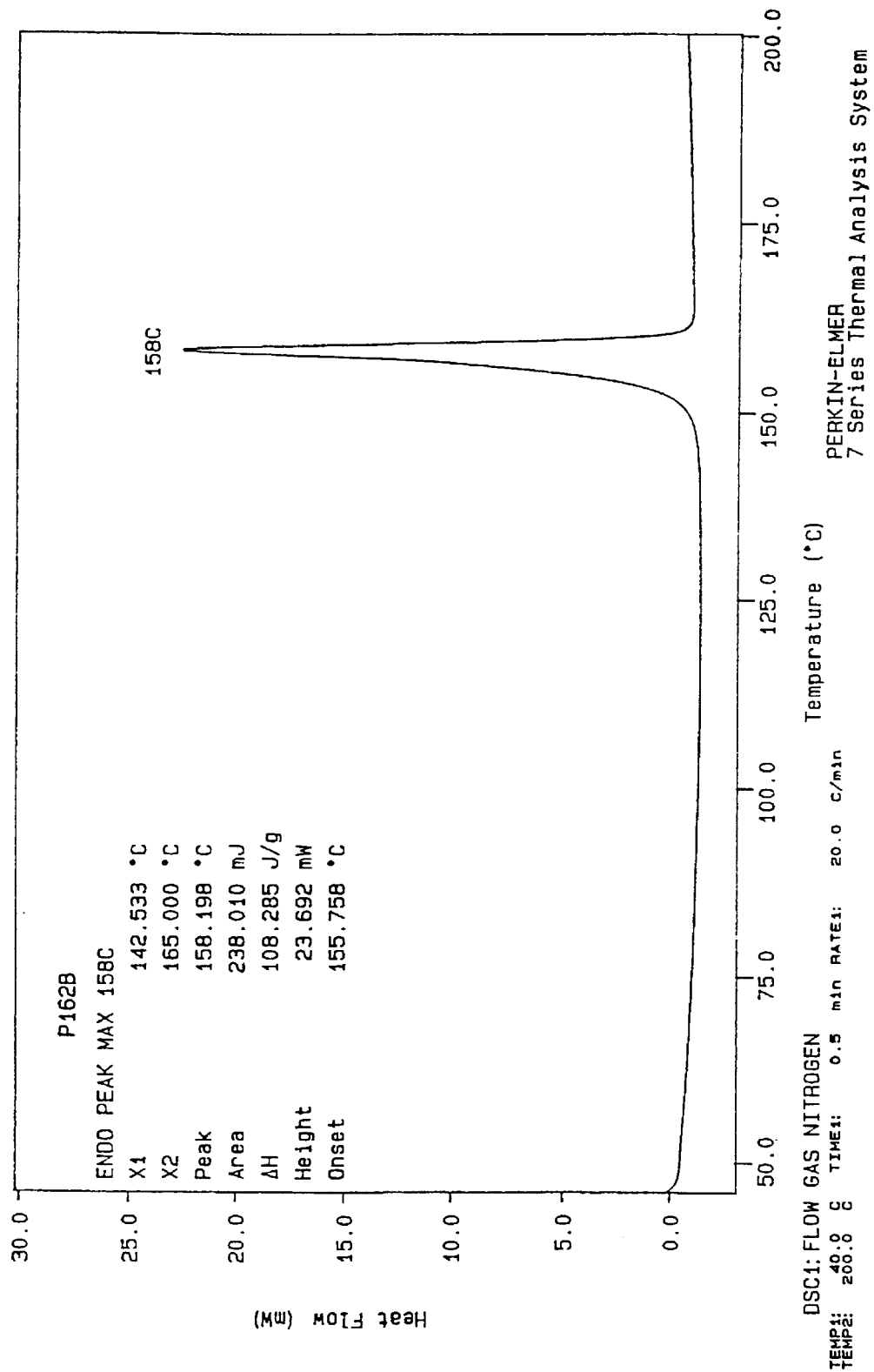

FIG. 10 shows the DSC thermogram for dofetilide polymorph P162b.

Figure 11:
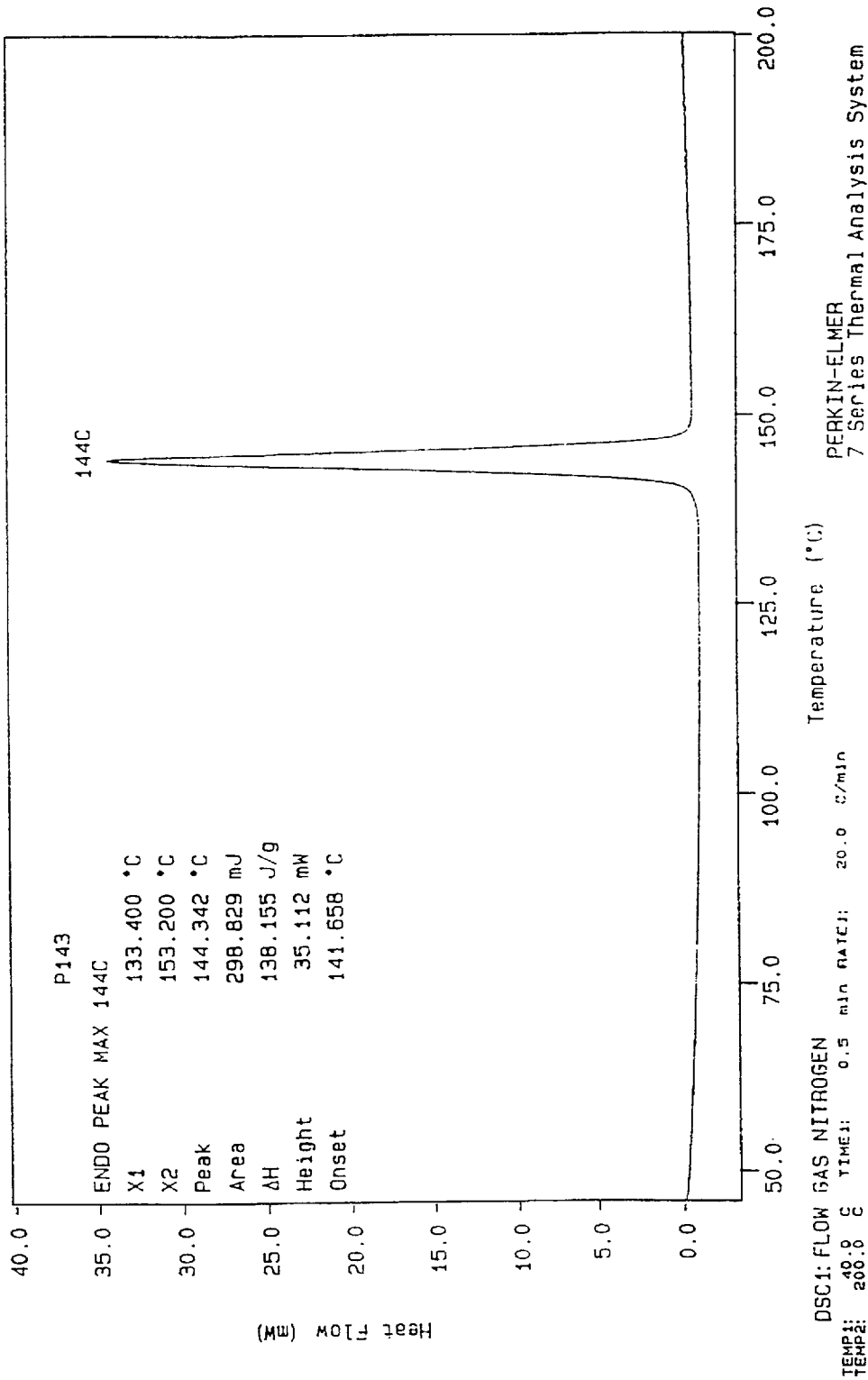

FIG. 11 shows the DSC thermogram for dofetilide polymorph P143.

Figure 12:
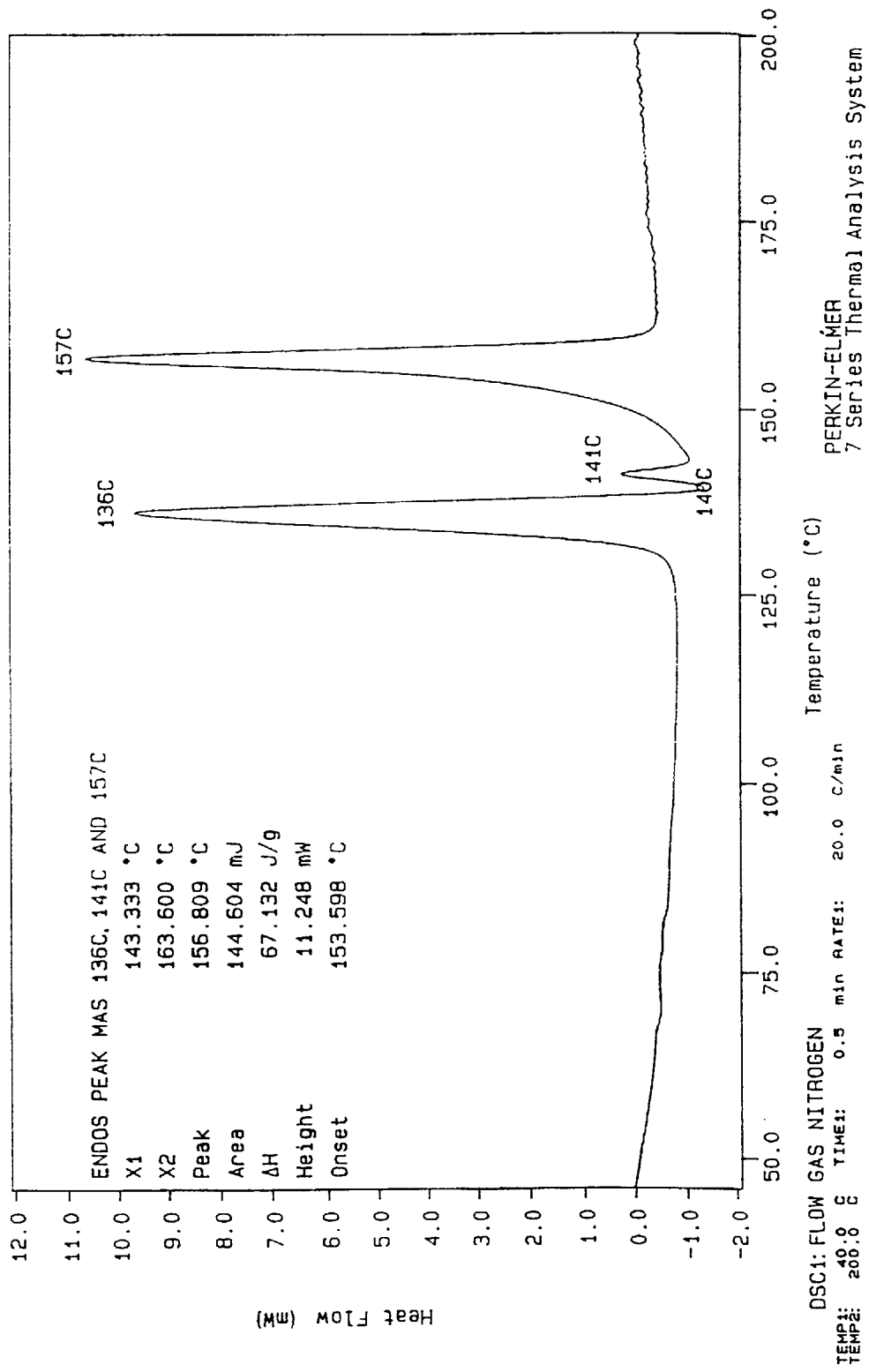

FIG. 12 shows the DSC thermogram for Reference Example 1.

Figure 12A:
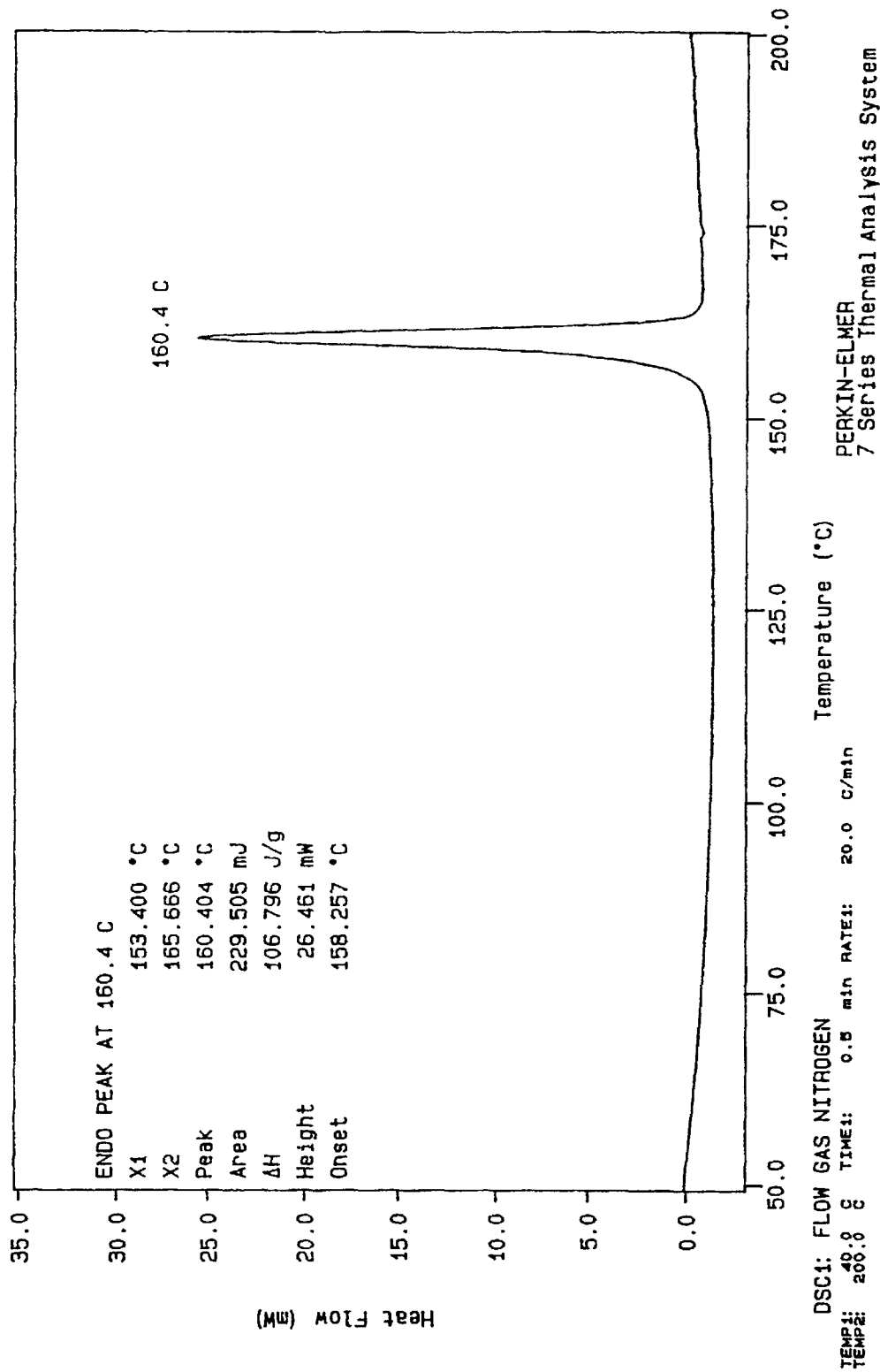

FIG. 12A shows the DSC thermogram for Reference Example 1A.

Figure 13:
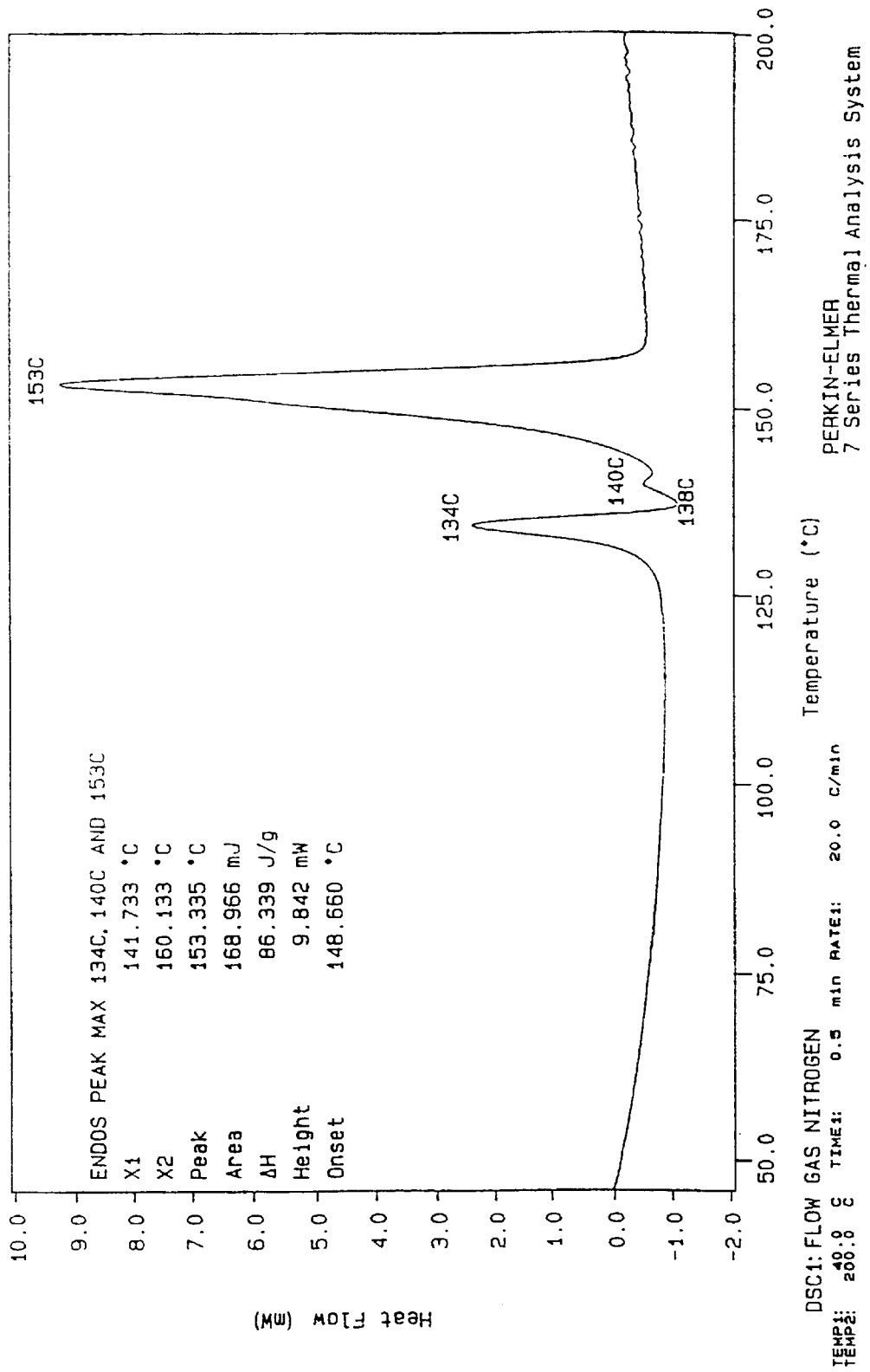

FIG. 13 shows the DSC thermogram for Reference Example 2.

FIG. 13A shows the DSC thermogram for Reference Example 2A.

Figure 14:
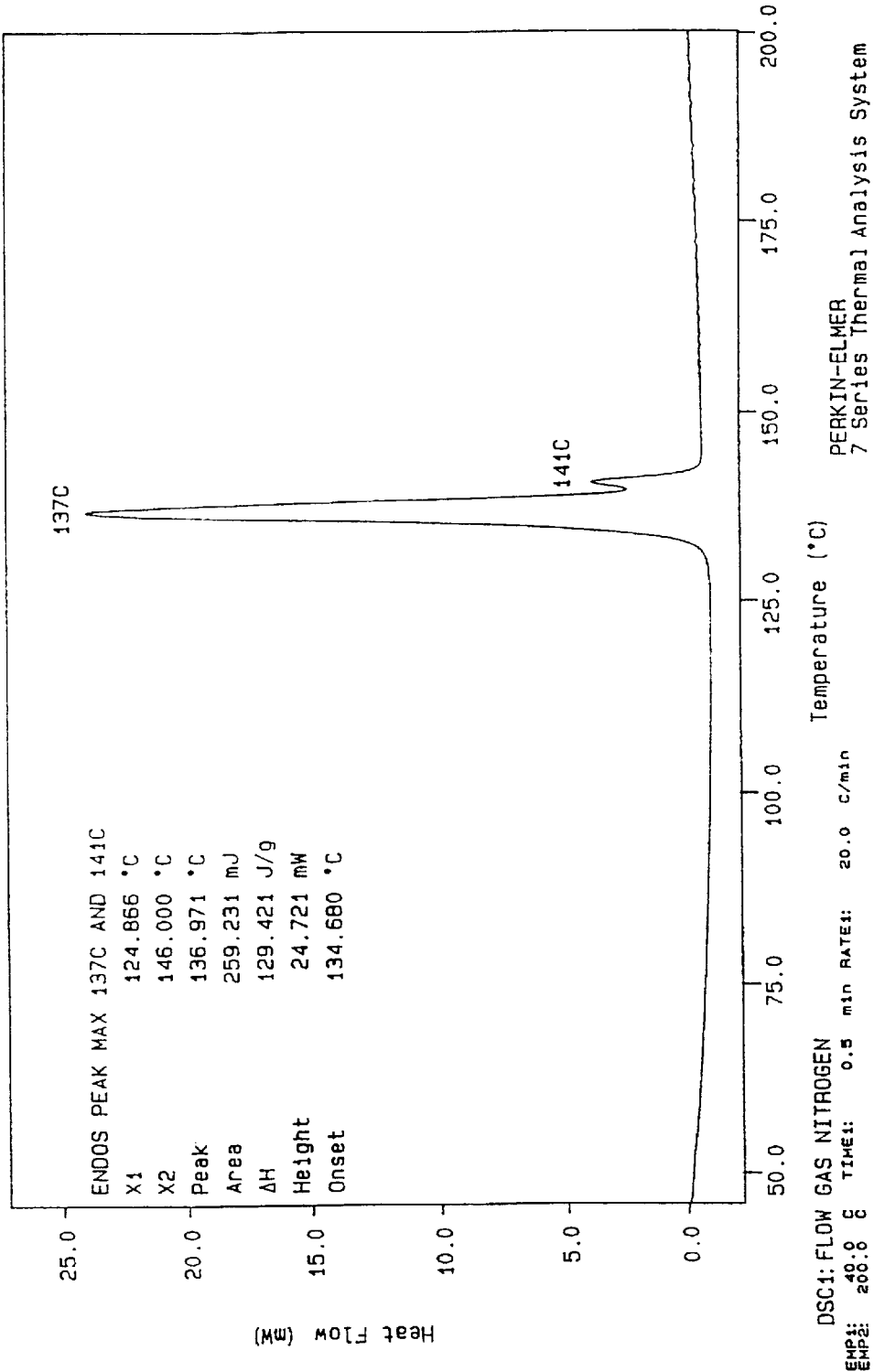

FIG. 14 shows the DSC thermogram for Reference Example 3.

Figure 14A:
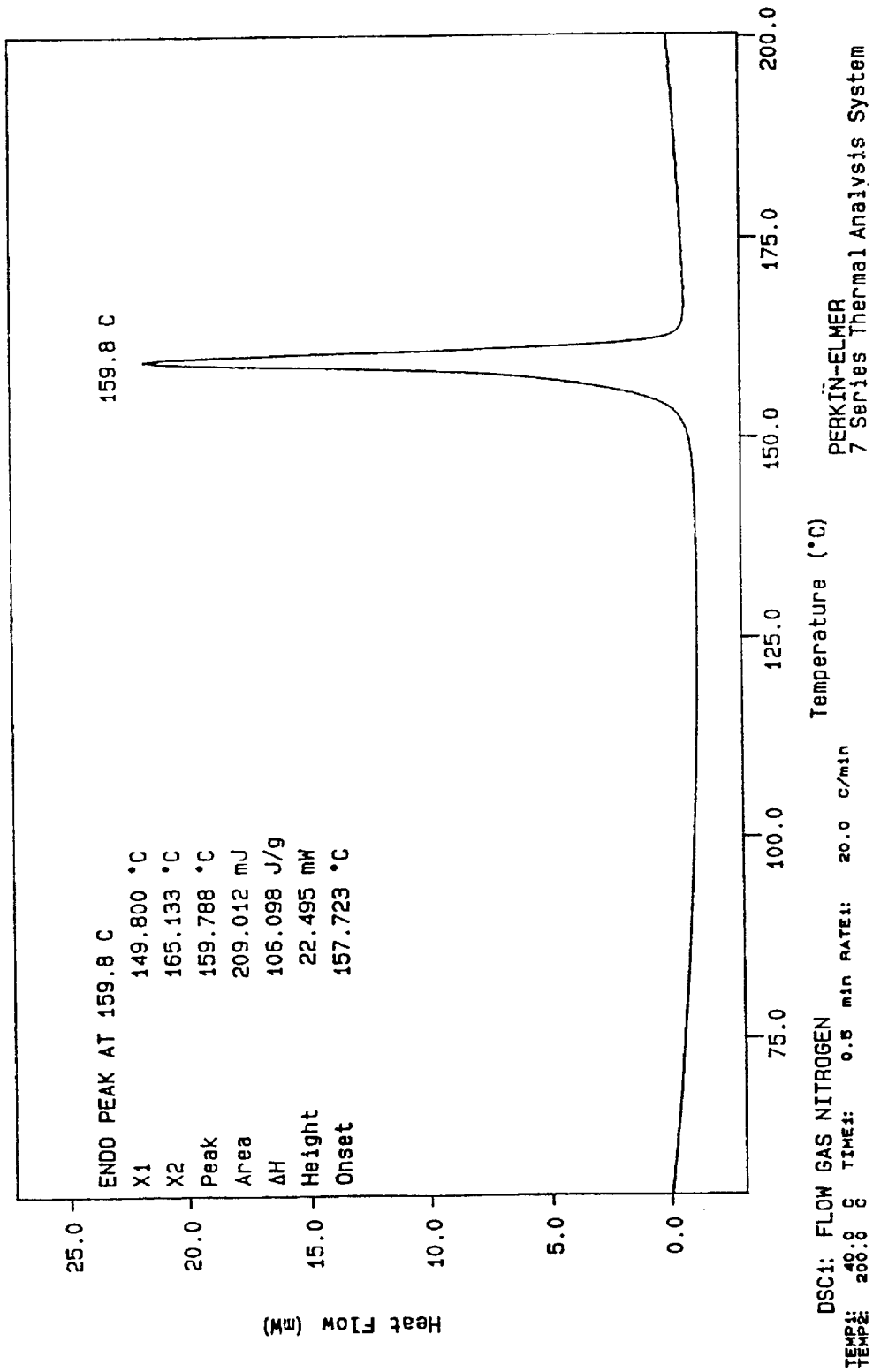

FIG. 14A shows the DSC thermogram for Reference Example 3A.

Figure 14B:
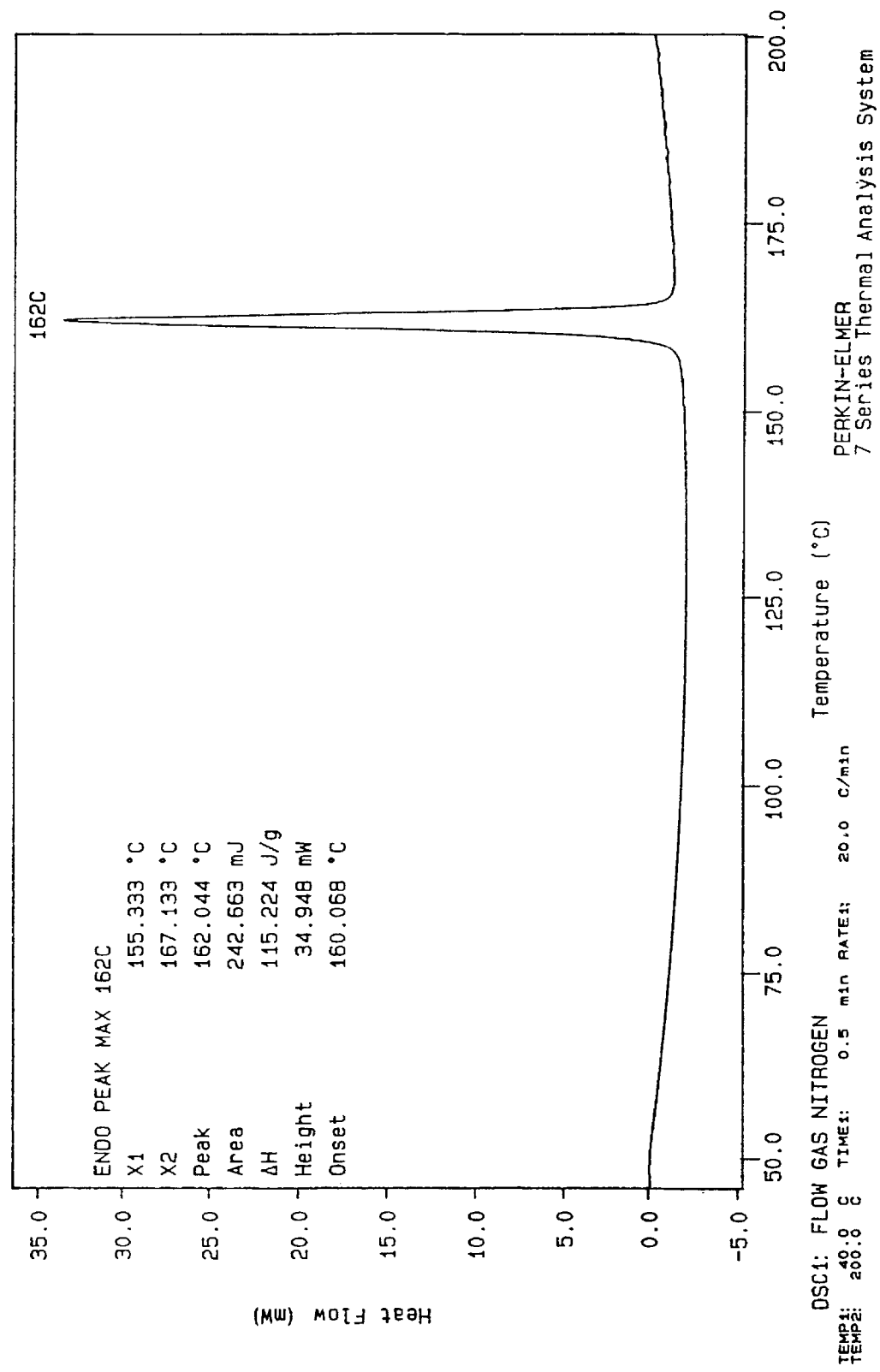

FIG. 14B shows the DSC thermogram for Example 6.

Figure 14C:
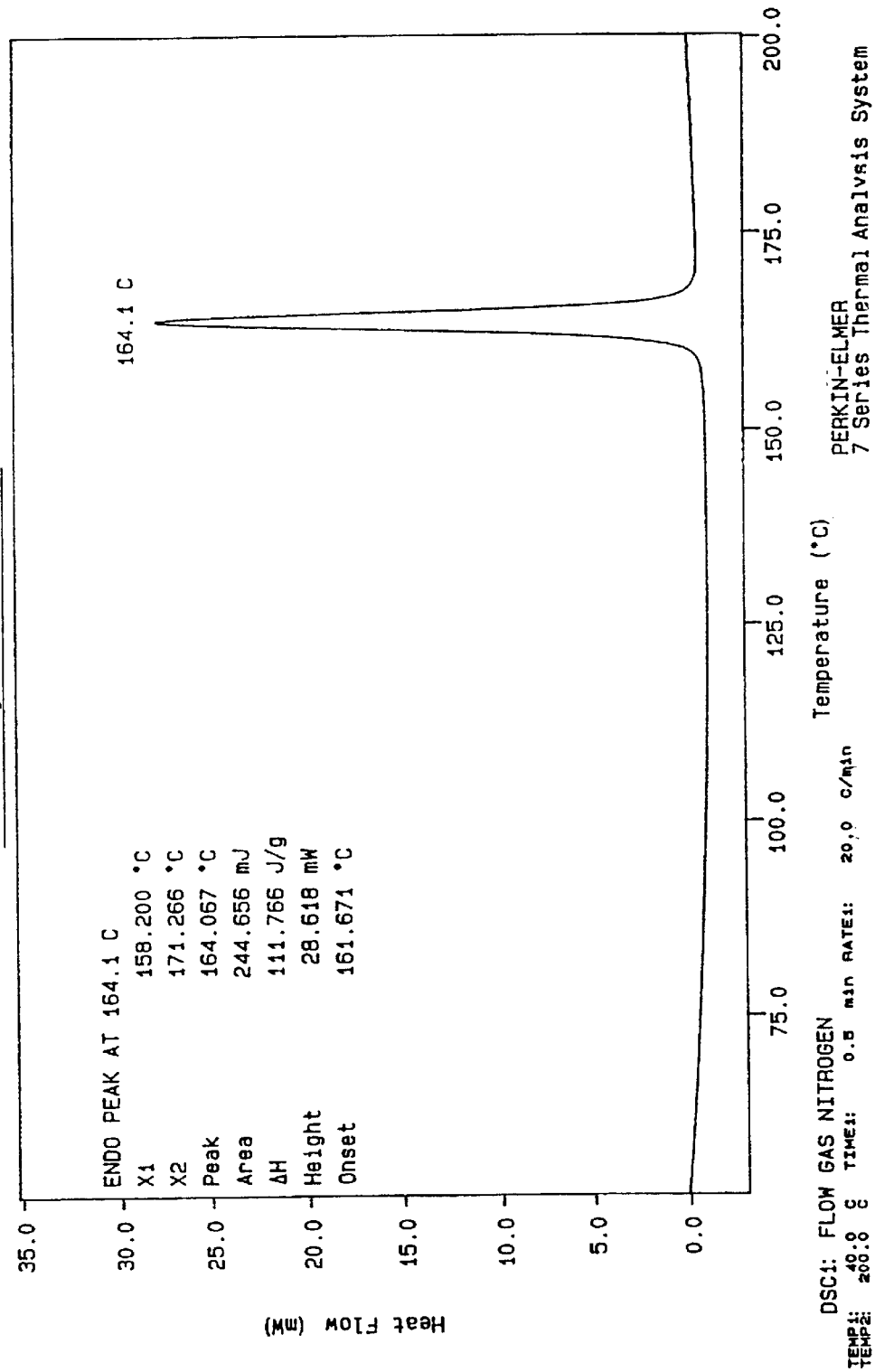

FIG. 14C shows the DSC thermogram for Example 7.

FIG. 14D shows the DSC thermogram for Example 8.

The thermal events for the above Figures are summarised in Table 2.

TABLE 2

| SAMPLE | THERMAL EVENTS |
|---|---|
| P162 | Peak = 162.5° C. (endotherm) |
| | Onset = 160.2° C. |
| | Enthalpy = 114.6 J/g |
| P162a | Peak = 159.8° C. (endotherm) |
| | Onset = 157.5° C. |
| | Enthalpy = 104.9 J/g |
| P162b | Peak = 158.2° C. (endotherm) |
| | Onset = 155.8° C. |
| | Enthalpy = 108.3 J/g |

TABLE 2-continued

| SAMPLE | THERMAL EVENTS | | | |
|---|---|---|---|---|
| P143 | Peak = 144.3° C. (endotherm) Onset = 141.6° C. Enthalpy = 138.2 J/g | | | |
| Reference Example 1 | Peak = 136.3° C. (endotherm) Onset = 132.0° C. Enthalpy = 56.3 J/g | Peak = 139.4° C. (exotherm) | Peak = 141.2° C. (endotherm) | Peak = 156.8° C. (endotherm) Onset = 153.6° C. Enthalpy = 67.1 J/g |
| Reference Example 2 | Peak = 134.4° C. (endotherm) Onset = 131.3° C. Enthalpy = 17.7 J/g | Peak = 137.4° C. (exotherm) | Peak = 139.8° C. (endotherm) | Peak = 153.3° C. (endotherm) Onset = 148.7° C. Enthalpy = 86.3 J/g |
| Reference Example 3 | Peak = 137.0° C. (endotherm) Onset = 134.7° C. Enthalpy = 129.4 J/g | Peak = 140.7° C. (endotherm) | | |
| Reference Example 1A | Peak 160.4° C. (endotherm) Onset 158.3° C. Enthalpy = 106.8 J/g | | | |
| Reference Example 2A | Peak 136.3° C. (endotherm) Onset 132.8° C. Enthalpy = 13.2 J/g | Peak = 143.5° C. (endotherm) Onset = 140.1° C. Enthalpy = 12.6 J/g | Peak = 153.4° C. (endotherm) Onset = 149.3° C. Enthalpy = 50.7 J/g | |
| Reference Example 3A | Peak 159.8° C. (endotherm) Onset = 157.7° C. Enthalpy = 106.1 J/g | | | |
| Example 6 | Peak = 162.0° C. (endotherm) Onset = 160.1° C. Enthalpy = 115.2 J/g | | | |
| Example 7 | Peak = 164.1° C. (endotherm) Onset = 161.7° C. Enthalpy = 111.8 J/g | | | |
| Example 8 | Peak = 162.8° C. (endotherm) Onset = 160.7° C. Enthalpy = 115.2 J/g | | | | c) IR

Infrared (IR) spectroscopy was performed on a Nicolet 800 FT-IR spectrometer fitted with an MCT-B detector. All spectra were acquired at 2 $cm^{-1}$ resolution. The samples were prepared as nujol mulls and mounted between two KBr plates prior to acquisition of the spectra.

Figure 15:
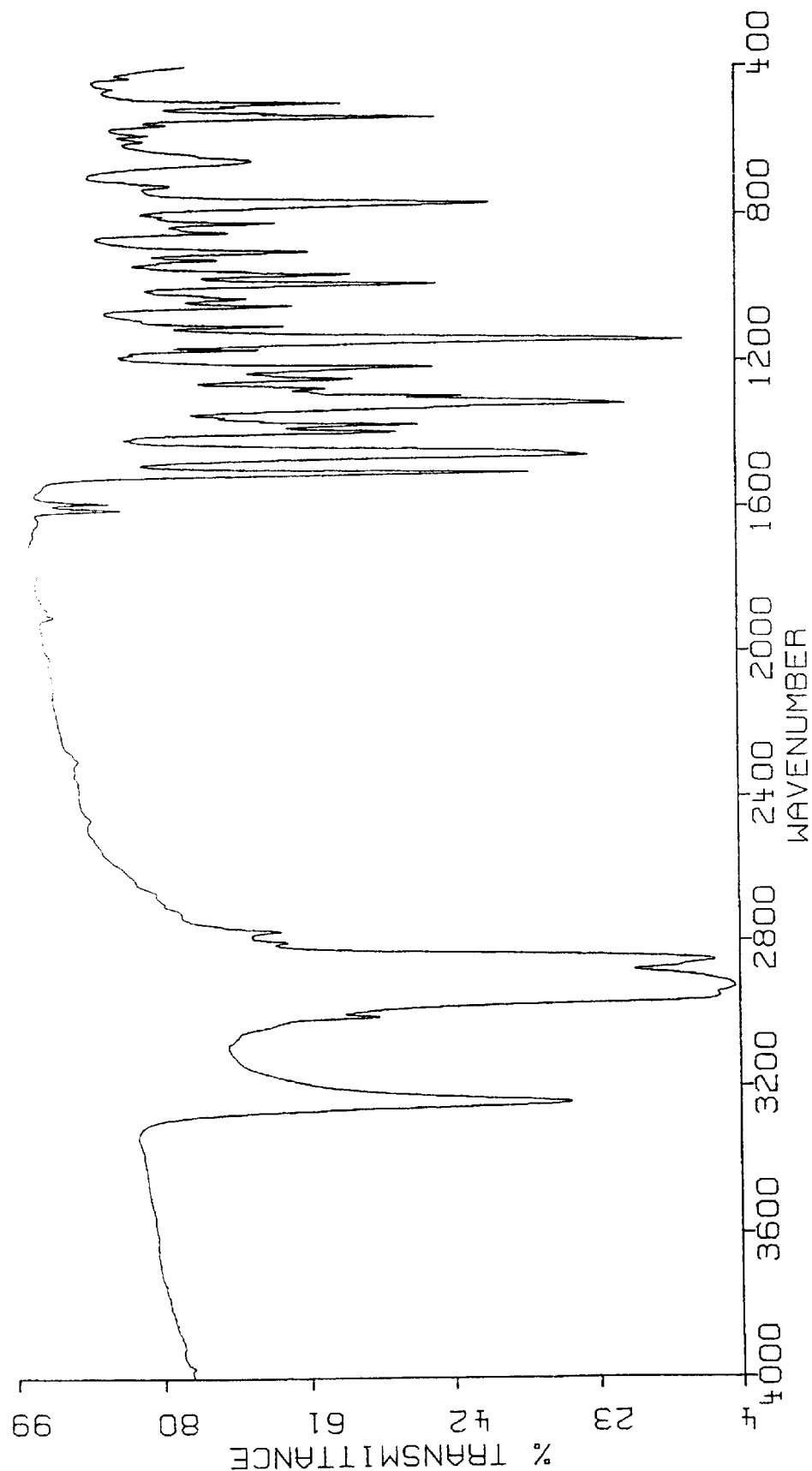
FIG. 15–21 are IR spectra for certain dofetilide polymorphs or mixtures thereof.

FIG. 15 shows the IR spectrum for dofetilide polymorph P162.

Figure 16:
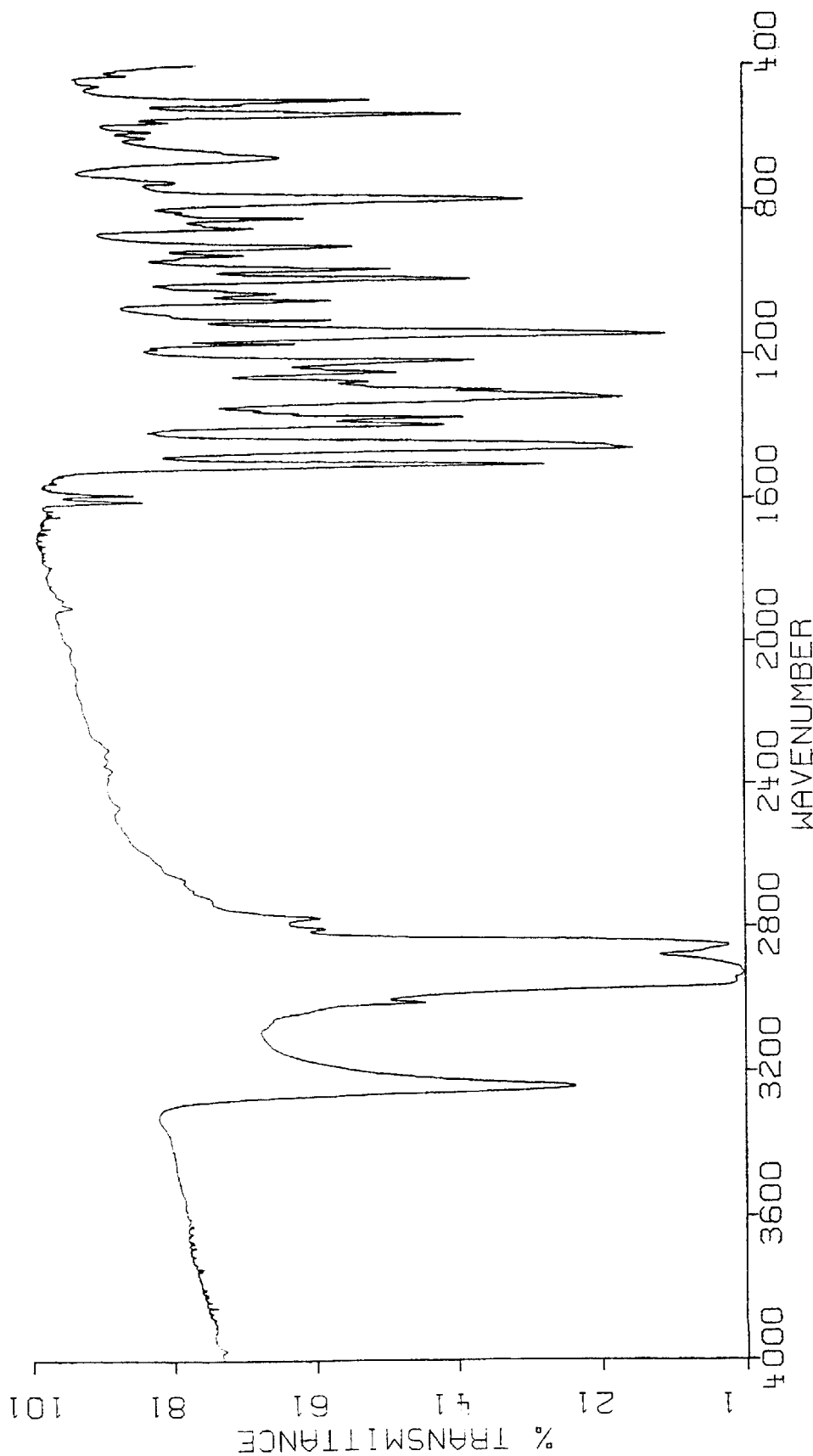

FIG. 16 shows the IR spectrum for dofetilide polymorph P162a.

Figure 17:
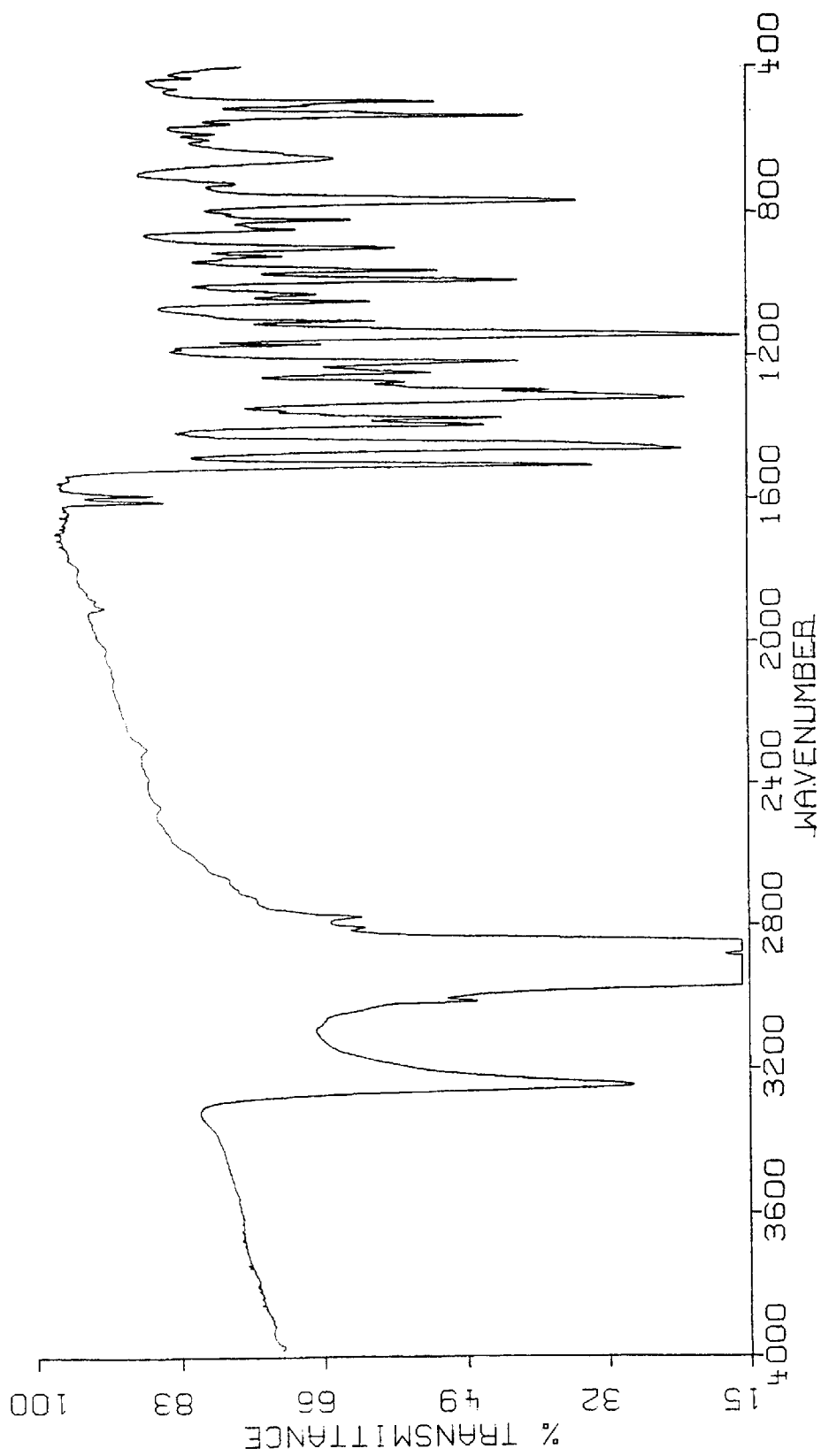

FIG. 17 shows the IR spectrum for dofetilide polymorph P162b.

Figure 18:
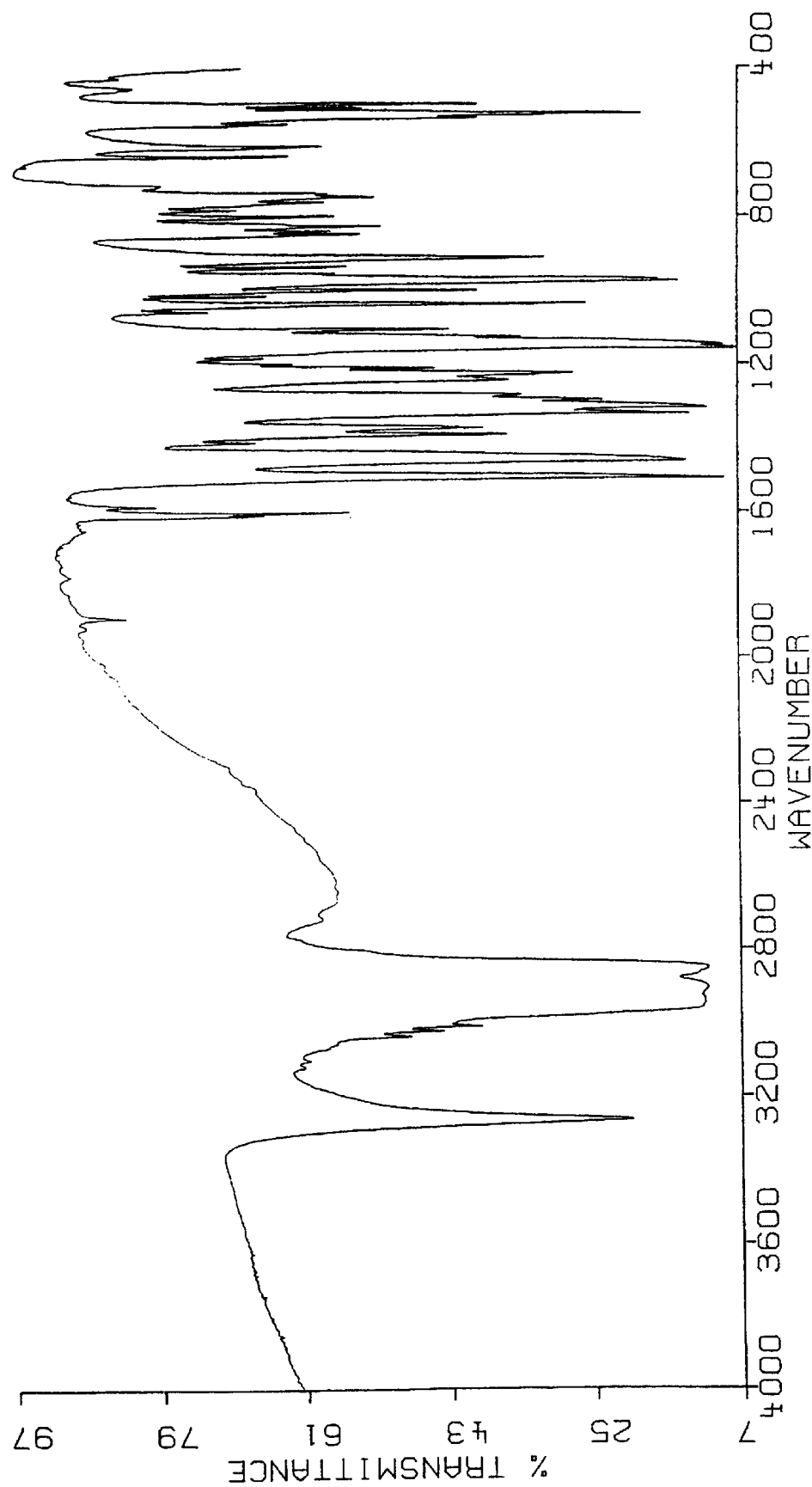

FIG. 18 shows the IR spectrum for dofetilide polymorph P143.

Figure 19:
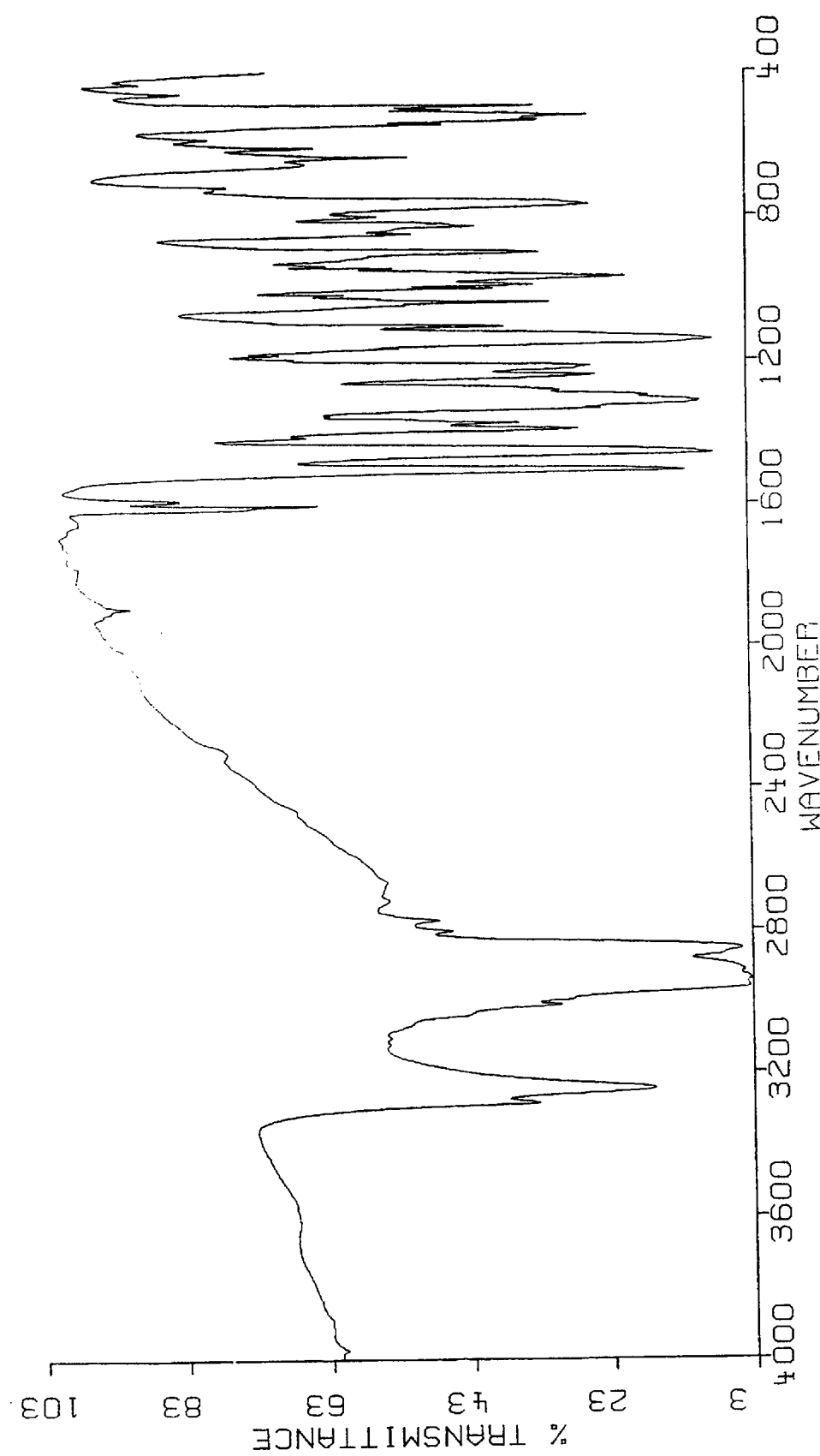

FIG. 19 shows the IR spectrum for Reference Example 1.

Figure 20:
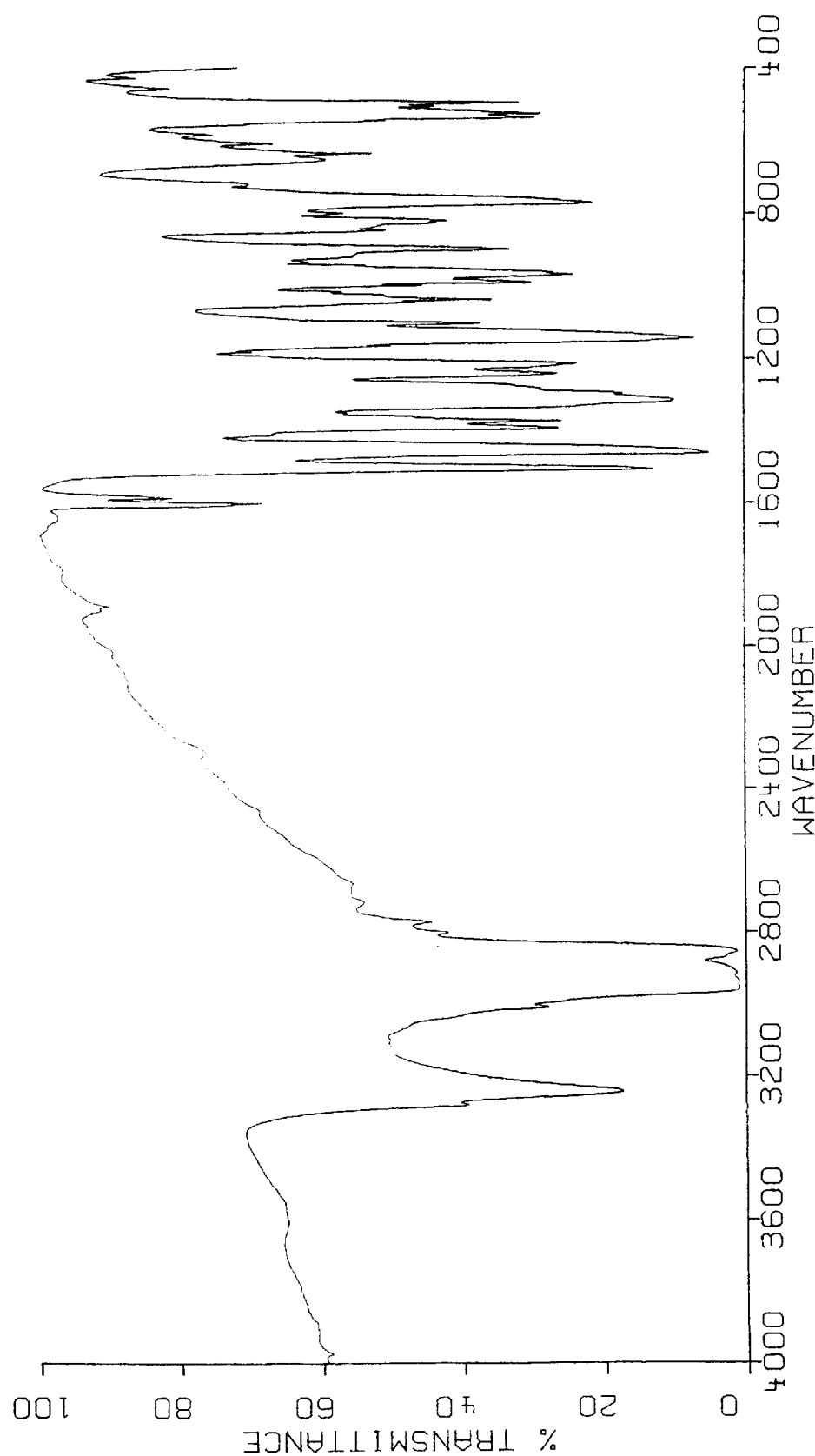

FIG. 20 shows the IR spectrum for Reference Example 2.

Figure 21:
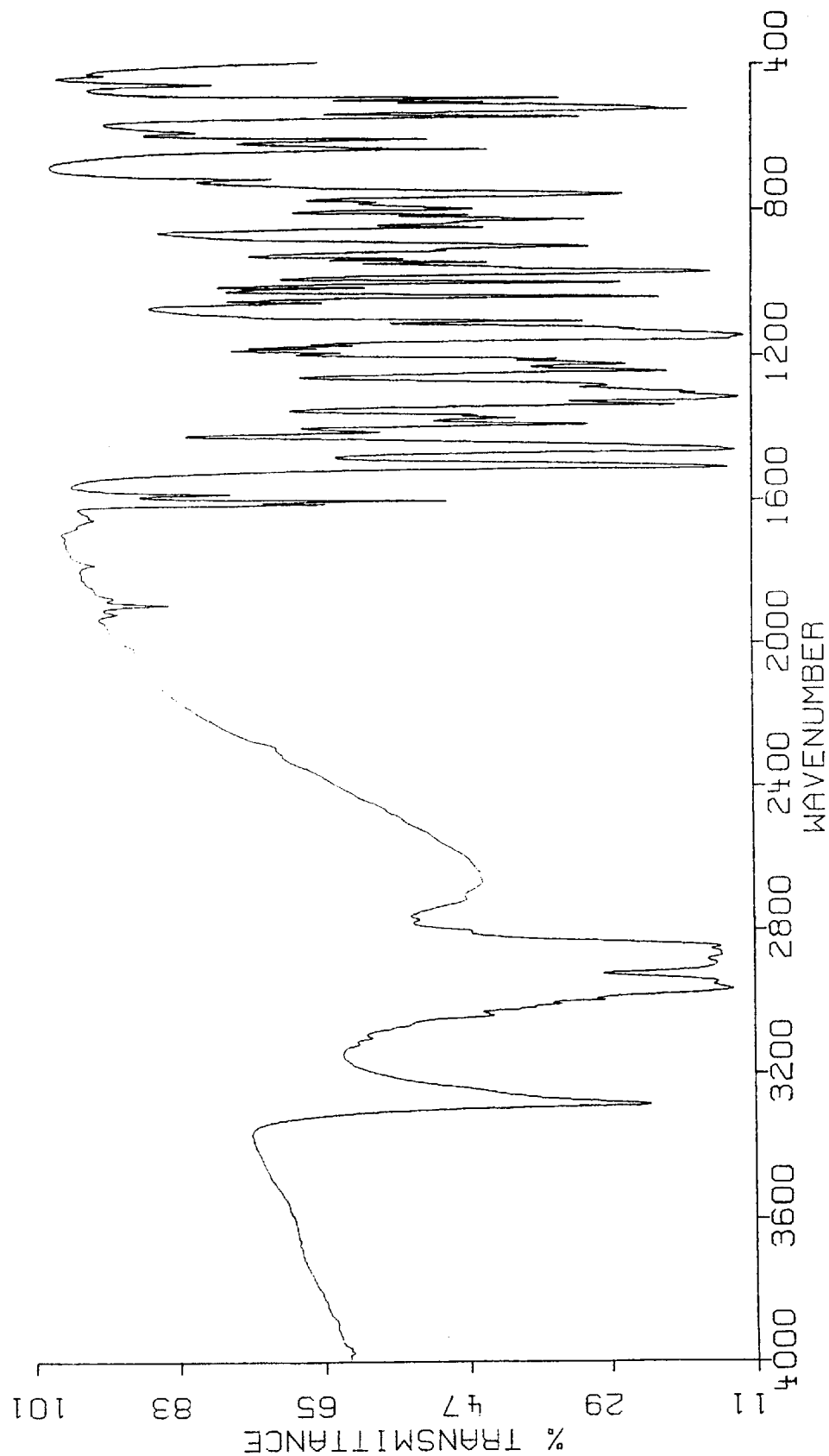

FIG. 21 shows the IR spectrum for Reference Example 3.

The peak listings for FIGS. 15 to 21 are shown in Table 3 in which the wavenumber ($cm^{-1}$) of each peak is recorded.

The peak listings for FIGS. 15 to 18 are also shown in Table 4 in which both the wavenumber ($cm^{-1}$) and percentage transmission (%T) of each peak are recorded.

TABLE 3

| P162 | P162a | P162b | P143 | Reference Example 1[1] | Reference Example 2[2] | Reference Example 3[3] |
|---|---|---|---|---|---|---|
| | | | | 3285.9 | 3284.8 | 3286.3 |
| | | | 3266.4 | | | |
| 3245.6 | 3245.6 | 3245.7 | | 3246.2 | 3246.0 | |
| | | | 3123.5 | | | 3123.0 |
| | | | 3106.7 | | | 3105.9 |
| | | | 3041.3 | | | 3042.8 |
| | | | 3026.7 | | | |
| 3012.8 | 3012.9 | 3012.6 | 3012.8 | 3011.5 | 3011.8 | 3010.1 |
| 2950–2850 nujol bands - Also see bands marked * | | | | | | |
| 2807.1 | 2807.1 | 2807.0 | | 2806.8 | 2807.0 | 2808.4 |
| 2776.2 | 2776.3 | 2776.2 | | 2776.4 | 2776.6 | 2774.9 |
| | | | 2766.5 | | | |
| | | | 2722.6 | 2721.0 | 2721.9 | |
| | | | ca. 2610 broad | ca. 2670 broad | ca. 2670 broad | ca. 2670 broad |
| 1907.1 | 1907.1 | 1906.7 | | | | |
| | | | | 1894.6 | 1894.8 | 1894.8 1894.8 |
| | | | | 1614.0 | 1613.6 | 1614.6 |
| 1610.7 | 1610.6 | 1610.5 | | | | |
| | | | | 1606.6 | 1606.0 | 1606.4 1605.9 |
| 1592.9 | 1592.9 | 1592.8 | | | 1592.7 | 1592.8 |
| | | | | 1587.1 | 1587.2 | 1587.6 1586.6 |
| 1510.0 | 1509.9 | 1509.7 | 1511.2 | 1510.4 | 1510.4 | 1510.6 |
| 1463.6* | 1463.7* | 1463.5* | 1464.4* | 1462.6* | 1462.7* | 1462.3* |

TABLE 3-continued

| P162 | P162a | P162b | P143 | Reference Example 1[1] | Reference Example 2[2] | Reference Example 3[3] |
|---|---|---|---|---|---|---|
|  |  |  | 1414.3 | 1415.6 | 1415.3 | 1416.0 |
| 1397.6 | 1397.3 | 1397.1 |  |  |  |  |
|  |  |  | 1395.4 | 1395.4 | 1395.9 | 1394.3 |
| 1377.7* | 1377.7* | 1377.7* | 1376.9* | 1377.8* | 1377.7* | 1377.1* |
| 1366.1 | 1366.1 | 1366.2 |  |  |  | 1369.3 |
| 1356.9 | 1356.8 | 1356.8 |  | 1356.5 | 1356.8 |  |
|  |  |  | 1337.3 | 1338.5 | 1338.1 | 1338.8 |
| 1321.4 | 1321.3 | 1321.2 |  |  |  |  |
|  |  |  | 1319.0 |  |  |  |
|  |  |  |  | 1316.3 | 1316.6 | 1315.9 |
|  |  |  | 1301.5 | 1301.8 | 1301.0 | 1302.9 |
| 1300.3 | 1300.2 | 1300.0 |  |  |  |  |
|  |  |  | 1287.4 | 1287.1 | 1288.0 | 1286.1 |
| 1276.8 | 1276.8 | 1276.6 |  |  |  |  |
| 1251.5 | 1251.2 | 1251.1 |  |  |  |  |
|  |  |  | 1248.0 |  |  |  |
|  |  |  |  | 1246.0 | 1246.3 | 1245.8 |
|  |  |  | 1230.5 |  |  |  |
|  |  |  |  |  |  | 1227.6 |
| 1219.9 | 1219.8 | 1219.6 |  | 1220.0 | 1219.9 |  |
|  |  |  | 1214.9 |  |  | 1215.1 |
|  |  |  | 1201.6 |  |  |  |
|  |  |  |  | 1197.7 |  | 1197.5 |
|  |  |  | 1186.8 | 1186.1 | 1186.0 | 1186.3 |
|  |  |  |  |  |  | 1177.4 |
| 1170.9 | 1171.0 | 1171.0 |  | 1170.7 | 1170.9 |  |
|  |  |  | 1157.0 |  |  |  |
|  |  |  |  |  |  | 1153.6 |
|  |  |  | 1148.3 |  |  |  |
| 1146.1 | 1146.0 | 1145.9 |  | 1146.2 | 1146.3 | 1146.3 |
|  |  |  | 1129.9 |  |  | 1130.1 |
|  |  |  | 1110.0 | 1109.7 |  | 1110.5 |
| 1106.4 | 1106.4 | 1106.2 |  |  | 1107.6 |  |
| 1091.3 | 1090.6 (sh) | 1089.6 (sh) |  |  |  |  |
|  |  |  | 1059.7 |  |  | 1059.7 |
|  |  |  |  | 1050.6 | 1051.0 |  |
|  |  |  | 1042.0 | 1042.9 | 1042.9 | 1042.9 |
| 1030.8 | 1031.4 | 1031.3 |  |  | 1032.6 |  |
| 1022.7 | 1022.8 | 1022.7 |  | 1023.7 | 1023.1 | 1024.1 |
|  |  |  | 1018.2 | 1019.5 | 1019.7 | 1019.3 |
|  |  |  | 1004.9 | 1004.9 | 1004.8 | 1005.1 |
| 993.9 | 993.8 | 993.5 |  | 993.9 | 993.9 |  |
|  |  |  | 979.6 |  |  |  |
|  |  |  | 975.0 | 973.4 | 973.5 | 973.5 |
| 966.0 | 965.7 | 965.6 |  |  | 966.1 |  |
|  |  |  | 958.9 |  |  |  |
|  |  |  |  | 949.0 | 949.2 | 948.8 |
|  |  |  | 940.2 | 939.1 | 939.1 | 939.5 |
| 934.1 | 934.0 | 933.9 |  |  |  |  |
| 925.5 | 925.6 | 925.4 |  |  | 924.6 |  |
|  |  |  | 917.1 | 917.7 | 917.8 | 917.4 |
|  |  |  |  | 904.1 | 903.9 | 904.8 |
| 903.5 | 903.4 | 903.2 |  |  |  |  |
|  |  |  |  |  | 853.3 | 854.3 |
| 851.3 | 851.2 | 851.2 | 852.6 |  | 852.1 |  |
|  |  |  | 844.4 |  |  |  |
|  |  |  | 831.5 | 831.8 | 831.5 | 832.0 |
|  |  |  |  | 826.6 | 825.3 |  |
| 824.8 | 824.9 | 824.8 |  |  |  |  |
|  |  |  |  |  |  | 820.1 |
| 807.8 | 807.4 | 807.4 |  |  |  |  |
|  |  |  | 803.1 | 804.0 | 804.5 | 803.6 |
|  |  |  | 784.8 |  |  | 786.4 |
| 774.4 | 774.0 | 773.7 |  | 773.9 | 774.0 |  |
|  |  |  | 765.9 |  |  |  |
|  |  |  |  |  |  | 762.2 |
|  |  |  | 752.3 |  |  |  |
|  |  |  | 742.7 |  |  |  |
|  | 725.7 (br) | 725.5 (br) |  |  |  |  |
| 722.6 (br) |  |  |  |  | 722.8 |  |
|  |  | 718.0 | 718.8 |  | 718.6 |  |
| 657.3 | 657.3 | 656.0 |  | 656.5 | 656.8 |  |
|  |  |  | 639.7 | 639.3 | 639.3 | 639.3 |
|  |  |  | 613.2 |  |  |  |
|  |  |  |  | 611.3 | 611.2 | 611.3 |
| 602.6 | 602.4 | 602.3 |  |  |  |  |
|  |  |  |  |  |  | 590.1 |
| 585.9 | 585.8 | 585.7 |  | 586.4 | 586.2 |  |
| 559.0 | 559.1 | 559.0 |  |  |  |  |
|  |  |  | 552.7 |  |  |  |
|  |  |  |  | 549.6 | 549.5 | 549.8 |
| 538.4 | 538.3 | 538.2 |  | 537.9 | 537.9 |  |
|  |  |  | 535.8 |  |  |  |
| 528.3 | 528.3 | 528.2 |  |  |  |  |
|  |  |  |  | 526.2 | 526.6 | 526.7 | 526.5 |
|  |  |  |  |  |  | 520.8 |
| 509.2 | 509.0 | 508.9 | 508.9 | 508.0 | 508.1 | 507.9 |
| 499.2 | 499.2 | 499.0 | 499.2 | 498.5 | 498.6 | 498.0 |
| 461.0 | 460.8 | 461.0 |  |  |  |  |
|  |  |  |  | 459.7 | 460.0 | 459.6 |
|  |  |  | 454.7 |  |  |  |
| 430.7 | 430.4 | 430.1 |  | 430.5 | 431.1 | 432.8 |
|  |  |  | 428.6 |  |  |  |

Footnotes
1. Dofetilide polymorph P136/P162b mixture.
2. Dofetilide polymorph P136/P162b mixture.
3. Dofetilide polymorph P136.

TABLE 4

| P162 | | P162a | | P162b | | P143 | |
|---|---|---|---|---|---|---|---|
| cm$^{-1}$ | % T | cm$^{-1}$ | % T | cm$^{-1}$ | % T | cm$^{-1}$ | % T |
|  |  |  |  |  |  | 3266.4 | 20.29 |
| 3245.6 | 26.38 | 3245.6 | 24.48 | 3245.7 | 28.87 |  |  |
|  |  |  |  |  |  | 3123.5 | 61.04 |
|  |  |  |  |  |  | 3106.7 | 60.37 |
|  |  |  |  |  |  | 3041.3 | 47.85 |
|  |  |  |  |  |  | 3026.7 | 43.83 |
| 3012.8 | 51.44 | 3012.9 | 45.31 | 3012.6 | 47.55 | 3012.8 | 39.10 |
| 2950–2850 nujol bands. Also see bands * | | | | | | | |
| 2807.1 | 63.58 | 2807.1 | 59.32 | 2807.0 | 60.75 |  |  |
| 2776.2 | 64.40 | 2776.3 | 60.01 | 2776.2 | 61.17 | 2766.5 | 63.25 |
|  |  |  |  |  |  | 2722.6 | 58.68 |
|  |  |  |  |  |  | ca 2610 broad | 57.13 |
| 1907.1 | 93.41 | 1907.1 | 94.68 | 1906.7 | 91.43 |  |  |
|  |  |  |  |  |  | 1894.6 | 82.75 |
|  |  |  |  |  |  | 1614.0 | 65.51 |
| 1610.7 | 84.73 | 1610.6 | 84.54 | 1610.5 | 84.22 |  |  |
|  |  |  |  |  |  | 1606.6 | 54.99 |
| 1592.9 | 86.23 | 1592.9 | 86.04 | 1592.8 | 85.52 |  |  |
|  |  |  |  |  |  | 1587.1 | 78.98 |
| 1510.0 | 31.50 | 1509.9 | 28.47 | 1509.7 | 33.45 | 1511.2 | 8.60 |
| 1463.6 * | 23.69 | 1463.7 * | 16.35 | 1463.5 * | 22.79 | 1464.4* | 13.24 |
|  |  |  |  |  |  | 1414.3 | 66.53 |
| 1397.6 | 48.61 | 1397.3 | 42.16 | 1397.1 | 46.46 |  |  |
|  |  |  |  |  |  | 1395.4 | 35.58 |
| 1377.7 * | 45.67 | 1377.7 * | 39.58 | 1377.7 * | 44.30 | 1376.9* | 38.60 |
| 1366.1 | 66.03 | 1366.1 | 62.58 | 1366.2 | 64.98 |  |  |
| 1356.9 | 71.07 | 1356.8 | 67.92 | 1356.8 | 69.75 |  |  |
|  |  |  |  |  |  | 1337.3 | 12.86 |
| 1321.4 | 18.68 | 1321.3 | 17.69 | 1321.2 | 22.36 |  |  |
|  |  |  |  |  |  | 1319.0 | 10.65 |
|  |  |  |  |  |  | 1301.5 | 23.60 |
| 1300.3 | 39.81 | 1300.2 | 34.27 | 1300.0 | 38.52 |  |  |
|  |  |  |  |  |  | 1287.4 | 33.75 |
| 1276.8 | 57.92 | 1276.8 | 52.77 | 1276.6 | 55.61 |  |  |
| 1251.5 | 54.32 | 1251.2 | 48.86 | 1251.1 | 52.56 |  |  |
|  |  |  |  |  |  | 1248.0 | 35.37 |
|  |  |  |  |  |  | 1230.5 | 27.28 |
| 1219.9 | 43.84 | 1219.8 | 37.96 | 1219.6 | 42.27 |  |  |
|  |  |  |  |  |  | 1214.9 | 44.47 |
|  |  |  |  |  |  | 1201.6 | 61.98 |

TABLE 4-continued

| P162 cm⁻¹ | P162 % T | P162a cm⁻¹ | P162a % T | P162b cm⁻¹ | P162b % T | P143 cm⁻¹ | P143 % T |
|---|---|---|---|---|---|---|---|
| | | | | | | 1186.8 | 65.50 |
| 1170.9 | 66.62 | 1171.0 | 62.74 | 1171.0 | 65.32 | | |
| | | | | | | 1157.0 | 7.06 |
| | | | | | | 1148.3 | 8.69 |
| 1146.1 | 10.87 | 1146.0 | 11.76 | 1145.9 | 15.56 | | |
| | | | | | | 1129.9 | 33.72 |
| | | | | | | 1110.0 | 42.71 |
| 1106.4 | 63.35 | 1106.4 | 57.85 | 1106.2 | 59.14 | | |
| 1091.3 | 81.66 | 1090.6 | 80.59 | 1089.6 | 78.73 | | |
| | | | | | | 1059.7 | 72.50 |
| 1051.4 | 62.12 | 1051.4 | 57.89 | 1051.3 | 59.76 | | |
| | | | | | | 1042.0 | 25.15 |
| 1030.8 | 68.18 | 1031.4 | 65.66 | 1031.3 | 66.06 | | |
| 1022.7 | 73.40 | 1022.8 | 72.44 | 1022.7 | 71.73 | | |
| | | | | | | 1018.2 | 65.16 |
| | | | | | | 1004.9 | 39.30 |
| 993.9 | 43.34 | 99.38 | 38.47 | 993.5 | 42.33 | | |
| | | | | | | 979.6 | 14.24 |
| | | | | | | 975.0 | 16.68 |
| 966.0 | 54.49 | 965.7 | 49.36 | 965.6 | 51.61 | | |
| | | | | | | 958.9 | 56.46 |
| | | | | | | 940.2 | 55.22 |
| 934.1 | 79.38 | 934.0 | 79.14 | 933.9 | 77.31 | | |
| 925.5 | 72.03 | 925.6 | 70.33 | 92.54 | 70.06 | | |
| | | | | | | 917.1 | 30.82 |
| 903.5 | 60.15 | 903.4 | 55.00 | 903.2 | 56.70 | | |
| 851.3 | 70.46 | 851.2 | 68.87 | 851.2 | 65.50 | 852.6 | 53.44 |
| | | | | | | 844.4 | 57.06 |
| | | | | | | 831.5 | 50.93 |
| 824.8 | 64.37 | 824.9 | 61.56 | 824.8 | 62.02 | | |
| 807.8 | 78.81 | 807.4 | 78.76 | 807.4 | 76.12 | | |
| | | | | | | 803.1 | 56.74 |
| | | | | | | 784.8 | 68.95 |
| 774.4 | 36.35 | 774.0 | 31.38 | 773.7 | 35.34 | | |
| | | | | | | 765.9 | 57.94 |
| | | | | | | 752.3 | 51.78 |
| | | | | | | 742.7 | 57.54 |
| | | 72.57 (br) | 79.71 | 725.5 (br) | 75.5 | | |
| 722.6 (br) | 77.86 | | | | | | |
| | | | | | | 718.0 | 78.20 |
| 657.3 | 67.41 | 657.3 | 65.23 | 656.0 | 640.7 | | |
| | | | | | | 639.7 | 61.93 |
| | | | | | | 613.2 | 58.32 |
| 602.6 | 81.33 | 602.4 | 84.03 | 602.3 | 78.67 | | |
| 585.9 | 80.63 | 585.8 | 83.12 | 585.7 | 77.98 | | |
| 559.0 | 78.39 | 559.1 | 80.71 | 559.0 | 76.17 | | |
| | | | | | | 552.7 | 62.39 |
| 538.4 | 43.29 | 538.3 | 39.69 | 538.2 | 41.72 | | |
| | | | | | | 535.8 | 39.14 |
| 528.3 | 64.08 | 528.3 | 62.37 | 528.2 | 60.02 | | |
| | | | | | | 526.2 | 18.67 |
| 509.2 | 69.57 | 509.0 | 70.43 | 508.9 | 66.94 | 508.9 | 53.06 |
| 499.2 | 55.62 | 499.2 | 52.44 | 499.0 | 52.02 | 499.2 | 38.97 |
| 461.0 | 85.33 | 460.8 | 90.56 | 461.0 | 82.53 | | |
| | | | | | | 454.7 | 81.65 |
| 430.7 | 83.14 | 430.4 | 86.76 | 430.1 | 80.77 | | |
| | | | | | | 428.6 | 83.40 | d) Particle size

Particle size analyses were performed by laser light diffraction using a Malvern Mastersizer S machine. Approximately 0.5 g of each sample was added to 100 ml of propan-2-ol, the resulting saturated solution filtered, further sample added and dispersed by ultrasonication followed by stirring. From triplicate determinations, the mean values for the particle size given by the D(v, 0.9) were calculated.

The particle size analyses obtained for dofetilide polymorph P162 and for each of the products of Reference Examples 1A, 2A and 3A are presented in Table 5.

TABLE 5

| SAMPLE | RESULT |
|---|---|
| Dofetilide polymorph P162 | 90% of particles less than 45 μm |
| Reference Example 1A[1] | 90% of particles less than 53 μm |
| Reference Example 2A[2] | 90% of particles less than 368 μm |
| Reference Example 3A | 90% of particles less than 14 μm |

Footnotes 1,2. Unlike for dofetilide polymorph P162, each of the products of Reference Examples 1A, 2A and 3A contained a mixture of fine material and large lumps that were up to 6–8 mm across. After sonication of each of the products of Reference Examples 1A, 2A and 3A in the saturated solution, many large lumps remained in the products of Reference Examples 1A and 2A and these were not included in the particle size analyses that were performed. As a result the particle size data obtained for the products of Reference Example 1A and 2A are not accurate since only the finer fractions were analysed The results presented in Table 5 show that in addition to dofetilide polymorph P162, only the product of Reference Example 3A had 90% of its particles with a size of less than 45 μm. However, the product of Reference Example 3A had 90% of its particles less than 14 μm which is regarded as too small to be suitable for use in a capsule formulation.

It should be noted that in order to remove the large lumps of material from the products of reference examples 1A, 2A and 3A, a milling step would be required in the manufacturing process that is unnecessary for dofetilide polymorph p162.

What is claimed is:

1. Substantially pure, crystalline, dofetilide polymorph P162 which is characterised by differential scanning calorimetry (DSC) in which it exhibits an endothermic thermal event at about 162° C.

2. Dofetilide polymorph P162 as claimed in claim 1 which is further characterised by a powder X-ray diffraction (PXRD) pattern obtained by irradiation with copper K-alpha$_1$ X-rays (wavelength=1.5406 Angstroms) which shows main peaks with interplanar spacings at dÅ 21.303, 10.597, 7.053, 5.288, 5.088, 4.856, 4.793, 4.569, 4.504, 4.430, 4.256, 4.230, 4.133, 3.956, 3.911, 3.866, 3.674, 3.606, 3.524, 3.424, 3.384, 3.309, 3.255, 3.171, 3.083, 3.038, 3.021, 2.893, 2.842, 2.776, 2.679, 2.598, 2.557, 2.503, 2.482, 2.436, 2.419, 2.399, 2.345 and 2.323.

3. Dofetilide polymorph P162 as claimed in claim 2 which is further characterised by an infrared (IR) spectrum as a mull in nujol which shows absorption bands at 3246, 3013, 2807, 2776, 1907, 1611, 1593, 1510, 1398, 1366, 1357, 1321, 1300, 1277, 1251, 1220, 1171, 1146, 1106, 1091, 1051, 1031, 1023, 994, 966, 934, 925, 903, 851, 825, 808, 774, 723, 657, 603, 586, 559, 538, 528, 509, 499, 461 and 431 cm⁻¹.

4. A process for the preparation of dofetilide polymorph P162 as claimed in claim 1 which comprises crystallisation of any other form of dofetilide, including mixtures thereof, from aqueous acetonitrile.

5. A process as claimed in claim 4 wherein from 98.5:1.5 to 99.5:0.5, by volume, acetonitrile:water is used.

6. A process as claimed in claim 5 wherein about 99:1, by volume, acetonitrile:water is used.

7. A pharmaceutical composition comprising dofetilide polymorph P162 as claimed in claim 1 together with a pharmaceutically acceptable diluent or carrier.

8. A composition as claimed in claim 7 which is a suitable for administration in a capsule dosage form.

9. A method of treating cardiac arrhythmia which comprises administering an effective amount of dofetilide polymorph P162 as claimed in claim 1 or a pharmaceutically acceptable composition thereof to an animal in need of such treatment.

10. A method of treating heart failure, particularly congestive heart failure, which comprises administering an effective amount of dofetilide polymorph P162 as claimed in claim 1 or a pharmaceutically acceptable composition thereof, to an animal in need of such treatment.

11. Substantially pure, crystalline, dofetilide polymorph P162a which is characterised by DSC in which it exhibits an endothermic thermal event at about 160° C.

12. Dofetilide polymorph P162a as claimed in claim 11 which is further characterised by a PXRD pattern obtained by irradiation with copper K-alpha$_1$ X-rays (wavelength= 1.5406 Angstroms) which shows main peaks with interplanar spacings at dÅ 21.306, 10.603, 7.054, 5.289, 5.114, 5.094, 4.860, 4.572, 4.431, 4.260, 4.247, 4.228, 4.153, 4.136, 3.955, 3.870, 3.676, 3.607, 3.524, 3.435, 3.421, 3.384, 3.176, 3.038, 2.895, 2.778, 2.684, 2.559, 2.501, 2.486, 2.433, 2.326, 2.283, 2.248, 2.216, 2.171, 2.119, 2.051, 1.989 and 1.948.

13. Dofetilide polymorph P162a is as claimed in claim 11 which is further characterised by an IR spectrum as a mull in nujol which shows absorption bands at 3246, 3013, 2807, 2776, 1907, 1611, 1593, 1510, 1397, 1366, 1357, 1321, 1300, 1277, 1251, 1220, 1171, 1146, 1106, 1091, 1051, 1031, 1023, 994, 966, 934, 926, 903, 851, 825, 807, 774, 726, 657, 602, 586, 559, 538, 528, 509, 499, 461 and 430 cm$^{-1}$.

14. A process for the preparation of dofetilide polymorph P162a as claimed in claim 11 which comprises dissolving any other form of dofetilide, including mixtures thereof, in an aqueous solution of a base, adjusting the solution to about pH 8.5 using an acid and collecting the product.

15. A process as claimed in claim 14 wherein the base is sodium hydroxide.

16. A process as claimed in claim 14 wherein the acid is a mineral acid such as hydrochloric acid.

17. Substantially pure, crystalline, dofetilide polymorph P143 which is characterised by DSC in which it exhibits an endothermic thermal event at about 144° C.

18. Dofetilide polymorph P143 as claimed in claim 17 which is further characterised by a PXRD pattern obtained by irradiation with copper K-alpha$_1$ X-rays (wavelength= 1.5406 Angstroms) which shows main peaks with interplanar spacings at dÅ 10.993, 9.006, 8.243, 6.769, 5.807, 5.530, 5.375, 5.104, 4.998, 4.735, 4.575, 4.539, 4.237, 4.179, 4.159, 4.019, 3.854, 3.705, 3.682, 3.601, 3.562, 3.482, 3.392, 3.343, 3.331, 3.263, 3.227, 3.173, 3.135, 3.082, 3.009, 2.946, 2.905, 2.859, 2.830, 2.803, 2.769, 2.672, 2.608 and 2.567.

19. Dofetilide polymorph P143 as claimed in claim 17 which is yet further characterised by an IR spectrum as a mull in nujol which shows absorption bands at 3266, 3123, 3107, 3041, 3027, 3013, 2766, 2723, 2610, 1895, 1614, 1607, 1587, 1511, 1414, 1395, 1337, 1319, 1301, 1287, 1248, 1230, 1215, 1202, 1187, 1157, 1148, 1130, 1110, 1060, 1042, 1018, 1005, 980, 975, 959, 940, 917, 853, 844, 831, 803, 785, 766, 752, 743, 718, 640, 613, 553, 536, 526, 509, 499, 455 and 429 cm$^{-1}$.

20. A process for the preparation of dofetilide polymorph P143 as claimed in claim 17 which comprises dissolving any other form of dofetilide, including mixtures thereof, in methanol, applying the solution obtained to a silica column, eluting the column with methanol and concentrating the eluted solution to dryness to provide the product.

21. A pharmaceutical composition comprising dofetilide polymorph P162a as claimed in claim 11 together with a pharmaceutical acceptable diluent or carrier.

22. A method of treating cardiac arrhythmia which comprises administering an effective amount of dofetilide polymorph P162a as claimed in claim 11 or a pharmaceutically acceptable composition thereof to an animal in need of such treatment.

23. A method of treating heart failure, particularly congestive heart failure, which comprises administering an effective amount of dofetilide polymorph P162a as claimed in claim 11 or a pharmaceutically acceptable composition thereof to an animal in need of such treatment.

24. A polymorph as claimed in claim 1 wherein substantially pure means at least 95% by weight pure.

25. A polymorph as claimed in claim 24 wherein substantially pure means at least 98% by weight pure.

26. A polymorph as claimed in claim 25 wherein substantially pure means at least 99% by weight pure.

27. A pharmaceutical composition comprising dofetilide polymorph P143 as claimed in claim 17 together with a pharmaceutical acceptable diluent or carrier.

28. A method of treating cardiac arrhythmia which comprises administering an effective amount of dofetilide polymorph P143 as claimed in claim 17 or a pharmaceutically acceptable composition thereof to an animal in need of such treatment.

29. A method of treating heart failure, particularly congestive heart failure, which comprises administering an effective amount of dofetilide polymorph P143 as claimed in claim 17 or a pharmaceutically acceptable composition thereof to an animal in need of such treatment.

\* \* \* \* \*